(12) United States Patent
Tsukumo

(10) Patent No.: US 11,103,251 B2
(45) Date of Patent: Aug. 31, 2021

(54) IN VIVO INDWELLING MEMBER, AND IN VIVO INDWELLING MEMBER PLACEMENT DEVICE PROVIDED WITH SAID IN VIVO INDWELLING MEMBER

(71) Applicant: KANEKA CORPORATION, Osaka (JP)

(72) Inventor: Kazutaka Tsukumo, Settsu (JP)

(73) Assignee: KANEKA CORPORATION, Osaka (JP)

( * ) Notice: Subject to any disclaimer, the term of this patent is extended or adjusted under 35 U.S.C. 154(b) by 283 days.

(21) Appl. No.: 15/982,320

(22) Filed: May 17, 2018

(65) Prior Publication Data

US 2018/0263630 A1    Sep. 20, 2018

Related U.S. Application Data

(63) Continuation-in-part of application No. PCT/JP2016/084365, filed on Nov. 18, 2016.

(30) Foreign Application Priority Data

Nov. 19, 2015    (JP) .............................. JP2015-226808

(51) Int. Cl.
*A61B 17/12* (2006.01)
*A61B 17/00* (2006.01)

(52) U.S. Cl.
CPC .. *A61B 17/12113* (2013.01); *A61B 17/12031* (2013.01); *A61B 17/12145* (2013.01);
(Continued)

(58) Field of Classification Search
CPC .......... A61B 17/1214; A61B 17/12145; A61B 17/1215; A61B 17/12154;
(Continued)

(56) References Cited

U.S. PATENT DOCUMENTS 5,645,558 A    7/1997    Horton
6,171,326 B1    1/2001    Ferrera et al.
(Continued)

FOREIGN PATENT DOCUMENTS

EP    0 765 636 A2    4/1997
JP    3024071 B2    3/2000
(Continued)

OTHER PUBLICATIONS

International Search Report (PCT/ISA/210) issued in PCT/JP2016/084365, dated Jan. 31, 2017.
(Continued)

*Primary Examiner* — Katherine H Schwiker
(74) *Attorney, Agent, or Firm* — Birch, Stewart, Kolasch & Birch, LLP

(57) ABSTRACT

The present invention relates to an in vivo indwelling member which has a shape complicatedly curved in various directions and can easily spread inside an aneurysm, while adhering to an inner wall of the aneurysm to prevent falling off therefrom, improving an indwelling density, and maintaining good operability. Shapes of two or more three-dimensional portions (middle solid 4A, large solid 4B) are provided in a primary coil 11. Each three-dimensional portion is formed by continuously providing at least four curved parts (51a to 51e/52a to 52f) over four planes. Normal directions of the four planes each have a relationship perpendicular to a predetermined common axis (a1/a2) direction. Each of the at least four curved parts (51a to 51e/52a to 52f) is formed on any of the respective planes of a quadrangular virtual cylindrical body as seen from the common axis (a1/a2) surrounded by the four planes.

12 Claims, 19 Drawing Sheets

(52) U.S. Cl.
CPC ........... *A61B 2017/00526* (2013.01); *A61B 2017/00867* (2013.01); *A61B 2017/12004* (2013.01); *A61B 2017/12068* (2013.01)

(58) Field of Classification Search
CPC .......... A61B 2017/12068; A61B 2017/12072; A61B 2017/12077; A61B 17/12022; A61B 17/12113; A61B 17/12118
See application file for complete search history.

(56) References Cited

U.S. PATENT DOCUMENTS

| | | | |
|---|---|---|---|
| 8,066,036 B2 * | 11/2011 | Monetti | A61B 17/1215 140/71 C |
| 2005/0090855 A1 | 4/2005 | Ferrera et al. | |
| 2014/0207180 A1 * | 7/2014 | Ferrera | A61L 31/022 606/200 |
| 2015/0057700 A1 * | 2/2015 | Chen | A61B 17/1214 606/200 |

FOREIGN PATENT DOCUMENTS

| | | |
|---|---|---|
| JP | 2004/500929 A | 1/2004 |
| JP | 3665133 B2 | 6/2005 |
| JP | 4065665 B2 | 3/2008 |

OTHER PUBLICATIONS

Written Opinion (PCT/ISA/237) issued in PCT/JP2016/084365, dated Jan. 31, 2017.

* cited by examiner

IN VIVO INDWELLING MEMBER, AND IN VIVO INDWELLING MEMBER PLACEMENT DEVICE PROVIDED WITH SAID IN VIVO INDWELLING MEMBER

CROSS-REFERENCE TO RELATED APPLICATIONS

This application is a Continuation-in-Part of PCT International Application No. PCT/JP2016/084365, filed on Nov. 18, 2016, which claims priority under 35 U.S.C. § 119(a) to Patent Application No. 2015-226808, filed in Japan on Nov. 19, 2015, all of which are hereby expressly incorporated by reference into the present application.

TECHNICAL FIELD

The present invention relates to an in vivo indwelling member suitable for treatment of an aneurysm or the like generated in a blood vessel, and to an in vivo indwelling member placement device provided with the in vivo indwelling member.

BACKGROUND ART

In treatment of an aneurysm generated in a blood vessel, there is adopted, for example, a method of embedding an in vivo indwelling member made of a metal coil into the aneurysm, thereby embolizing the aneurysm, and preventing a rupture of the aneurysm. As the metal coil which is the in vivo indwelling member, there is used a secondary coil shaped to a three-dimensional secondary shape, which is formed by processing a wire of platinum or the like into a coil shape to form a primary coil, and further, bending the primary coil into the secondary shape by heating. Such a metal coil (secondary coil) is inserted into a lumen of a catheter for delivery in a state of being extended in the shape of the primary coil, is delivered to a target part together with the catheter, is pushed out from the catheter by an indwelling operation, and is indwelled in the aneurysm in a state of being developed into a secondary shape or in a state of being along a shape of the aneurysm.

To embolize the aneurysm, it is considered advantageous to spread the metal coil in various directions without confining the metal coil at one site in an inside of the aneurysm. Therefore, desirably, the secondary shape (shape of the secondary coil) to be imparted to the metal coil is a shape which is complicatedly curved in various directions along a wall of the aneurysm and easily spreads into the aneurysm when the coil is developed in the aneurysm. Accordingly, various secondary coils having such a complicated three-dimensional shape and various methods for manufacturing the secondary coil have been conventionally proposed.

For example, Patent Literatures 1 to 3 have proposed secondary coils, each of which has a secondary shape extending on a substantially spherical or elliptical spherical surface while being curved in various directions. Each of these secondary coils is given the secondary shape by being heated in a state in which the primary coil is looped around an outer surface of a substantially spherical or elliptical spherical core. In each of Patent Literatures, the shape of the secondary coil is a three-dimensional shape in which loop-shaped parts obtained by looping the primary coil complicatedly intersect one another many times. In addition, shape memory alloys and superelastic materials are often used as a material of the coil.

When the loop-shaped parts of the primary coil intersect one another many times to form the three-dimensional shape as described above, the metal coil is restored to a spherical shape having many loops in the aneurysm. Therefore, while the metal coil can be prevented from being confined at one site, the three-dimensional shape thereof restored inside the aneurysm or the like has high shape retention, and the metal coil has a limit to adhesion with an inner wall of the aneurysm that originally has not the spherical inner surface shape but a variety of inner surface shapes. Then, there are problems that gaps are increased and that an indwelling density of the coil into the inside of the aneurysm cannot be raised.

In addition, in such an indwelling operation of indwelling the metal coil inside the aneurysm or the like, the metal coil is not pushed out into the aneurysm at one time, but is gradually pushed out so as to spread out while being slightly returned in the middle of the operation. However, in the above-described metal coil in which the three-dimensional shape is restored, the loop-shaped parts thus pushed out are likely to be entangled with one another, and especially, operability in returning the metal coil is adversely affected.

In addition, in Patent Literature 4, a secondary shape is proposed, in which loop-shaped parts similar to those of the primary coils are arranged on respective surfaces of a virtual cube. In such a secondary shape, the loop-shaped parts are positioned away from one another. Therefore, as compared with three-dimensional shapes of Patent Literatures 1 to 3 described above, the loop-shaped parts in Patent Literature 4 are less likely to interfere with one another, and have a shape that is more likely to adhere to the inner wall of the aneurysm due to deformation.

However, also in the metal coil in Patent Literature 4, a cuboid shape in which the loop-shaped parts are mutually supported from six directions is restored and maintained. Therefore, the metal coil in Patent Literature 4 has limits to the above flexible deformation, improvement of the adhesion to the inner wall of the aneurysm, and improvement of indwelling density of the coil. Moreover, it is highly likely that the above-described operability is adversely affected. Therefore, such an in vivo indwelling member has been required, which is capable of further improving the adhesion and the indwelling density and is also capable of maintaining good operability.

CITATIONS LIST

Patent Literatures

Patent Literature 1: Japanese Patent No. 3665133
Patent Literature 2: Japanese Patent No. 3024071
Patent Literature 3: JP-T No. 2004-500929
Patent Literature 4: Japanese Patent No. 4065665

SUMMARY OF INVENTION

Technical Problems

The present invention has been made in view of the above-mentioned circumstances. It is an object of the present invention to provide an in vivo indwelling member which, while having a shape complicatedly curved in various directions along the aneurysm wall and easily spreading inside the aneurysm or the like, is capable of being adhered to the inner wall of the aneurysm or the like to be prevented from falling off therefrom, is also capable of further improving the indwelling density, and is capable of maintaining good operability. It is another object of the present invention to provide an in vivo indwelling member placement device provided with the in vivo indwelling member.

Solutions to Problems

That is, the present invention includes the following inventions.

(1) An in vivo indwelling member having a three-dimensional secondary shape in which shape parts (hereinafter, referred to as "curved parts" in this specification) of a primary coil, the shape parts extending continuously and curvedly on substantially a same plane, are formed on two or more planes, the in vivo indwelling member including two or more three-dimensional portions, each of the three-dimensional portions being formed by continuously providing at least four of the curved parts over four planes, all of the four planes having normal directions perpendicular to a predetermined common axis direction, each of the at least four shape parts being formed in any of respective planes of a virtual cylindrical body having a shape of a quadrangle as seen from the common axis surrounded by the four planes, the three-dimensional portions being set so that areas of the quadrangles as seen from the common axes of the virtual cylindrical bodies of the two or more three-dimensional portions are sequentially changed from a tip end side of the primary coil toward a base end side of the primary coil, and a length of the primary coil that constitutes the three-dimensional portion excluding the three-dimensional portion disposed closest to the base end side being set to a length of 25% or more and 70% or less of an overall length of the primary coil. Here, the term "tip end side" refers to a distal side which is previously pushed out to the aneurysm or the like, and the term "base end side" refers to a proximal side which is pushed out later.

(2) An in vivo indwelling member having a three-dimensional secondary shape in which curved parts of a primary coil, the curved parts extending continuously and curvedly on substantially a same plane, are formed on two or more planes, the in vivo indwelling member including two or more three-dimensional portions, each of the three-dimensional portions being formed by continuously providing at least four of the curved parts over four planes, all of the four planes having normal directions perpendicular to a predetermined common axis direction, each of the at least four curved parts being formed in any of respective planes of a virtual cylindrical body having a shape of a quadrangle as seen from the common axis surrounded by the four planes, the three-dimensional portions being set, in order from a tip end side toward a base end side of the primary coil, so that the three-dimensional portion having a relatively small area of the quadrangle as seen from the common axes of the virtual cylindrical bodies is disposed on the tip end side, and that the three-dimensional portion having a relatively large area of the quadrangle as seen from the common axes of the virtual cylindrical bodies is disposed on the base end side, and a length of the primary coil that constitutes the three-dimensional portion excluding the largest three-dimensional portion being set to a length of 25% or more and 50% or less of an overall length of the primary coil. Here, the term "tip end side" refers to a distal side which is previously pushed out to the aneurysm or the like, and the term "base end side" refers to a proximal side which is pushed out later.

(3) The in vivo indwelling member according to (2), in which an anchor portion formed of at least one of the curved parts is provided in a region of the primary coil, the region leading to a tip of the primary coil more on a tip end side than the smallest three-dimensional portion, and a length of the primary coil that constitutes the anchor portion is set to a length of less than 15% of the overall length of the primary coil.

(4) An in vivo indwelling member having a three-dimensional secondary shape in which curved parts of a primary coil, the curved parts extending continuously and curvedly on substantially a same plane, are formed on two or more planes, the in vivo indwelling member including two or more three-dimensional portions, each of the three-dimensional portions being formed by continuously providing at least four of the curved parts over four planes, all of the four planes having normal directions perpendicular to a predetermined common axis direction, each of the at least four curved parts being formed in any of respective planes of a virtual cylindrical body having a shape of a quadrangle as seen from the common axis surrounded by the four planes, the three-dimensional portions being set so that the three-dimensional portion having a relatively large area of the quadrangle as seen from the common axes of the virtual cylindrical bodies is disposed on a tip end side of the primary coil, and that the three-dimensional portion having a relatively small area of the quadrangle as seen from the common axes of the virtual cylindrical bodies is disposed on a base end side of the primary coil, and a length of the primary coil that constitutes the three-dimensional portion excluding the smallest three-dimensional portion being set to a length of 25% or more and 70% or less of an overall length of the primary coil. Here, the term "tip end side" refers to a distal side which is previously pushed out to the aneurysm or the like, and the term "base end side" refers to a proximal side which is pushed out later.

(5) The in vivo indwelling member according to (4), in which an anchor portion formed of at least one of the curved parts is provided in a region of the primary coil, the region leading to a tip of the primary coil more on a tip end side than the largest three-dimensional portion, and a length of the primary coil that constitutes the anchor portion is set to a length of less than 15% of the overall length of the primary coil.

(6) The in vivo indwelling member according to any one of (1) to (5), in which with regard to a ratio of the areas of the three-dimensional portion having a relatively small area of the quadrangle as seen from the common axis of the virtual cylindrical body and of the three-dimensional portion having a next large area of the quadrangle as seen from the common axis of the virtual cylindrical body, the ratio is set so that the area of the large three-dimensional portion is 1.1 times or more and 2.3 times or less the area of the small three-dimensional portion.

(7) The in vivo indwelling member according to any one of (1), (2) and (4), in which with regard to a ratio of shortest side that constitutes the quadrangle of the three-dimensional portion having a relatively small area of the quadrangle as seen from the common axis of the virtual cylindrical body and of a shortest side that constitutes the quadrangle of the three-dimensional portion having a next large area of the quadrangle as seen from the common axis of the virtual cylindrical body, the ratio is set so that the length of the large three-dimensional portion is 1.05 times or more and 1.5 times or less the length of the small three-dimensional portion.

(8) The in vivo indwelling member according to any one of (1) to (7), in which the quadrangles as seen from the common axes of the virtual cylindrical bodies are squares.

(9) The in vivo indwelling member according to any one of (1) to (8), in which the four or more curved parts are formed in any of the planes which are the squares of each of the virtual cylindrical bodies.

(10) The in vivo indwelling member according to any one of (1) to (9), in which another solid is disposed inside one of the solids, and the common axes of the respective solids are parallel to each other.

(11) The in vivo indwelling member according to (10), in which the three-dimensional portion smaller than the largest three-dimensional portion is disposed inside the largest three-dimensional portion, and the common axes of the respective three-dimensional portions are parallel to each other.

(12) An in vivo indwelling member placement device including: an in vivo indwelling member placement wire; the in vivo indwelling member according to any one of (1), (2) and (4); and a cuttable coupling member that couples the wire and the in vivo indwelling member to each other.

(13) The in vivo indwelling member placement device according to (12), in which the coupling member is formed of a thermally soluble material.

(14) A method for producing an in vivo indwelling member having a three-dimensional secondary shape in which shape parts of a primary coil, the shape parts extending continuously and curvedly on substantially a same plane, are formed on two or more planes, the method comprising:
  providing a wire;
  winding the wire around a linear mandrel and removing the linear mandrel therefrom so that the wire is formed into a primary coil;
  inserting a core wire into a lumen of the primary coil;
  winding the primary coil around a mandrel having a winding portion so that the primary coil is formed into an intermediate shape, the intermediate shape comprising two or more three-dimensional portions, each of the three-dimensional portions being formed by continuously providing at least four of the shape parts over four planes, all of the four planes having normal directions perpendicular to a predetermined common axis direction, each of the at least four shape parts being formed in any of respective planes of a virtual cylindrical body having a shape of a quadrangle as seen from the common axis surrounded by the four planes,
  heating the primary coil wound on the mandrel at 400° C. or higher for 15 minutes or longer;
  removing the primary coil from the mandrel;
  placing the primary coil into a lumen of a mold; and
  heating the primary coil in the lumen of the mold at 400° C. or higher for 15 minutes or longer at 400° C. or higher for 15 minutes or longer to form a secondary shape.

(15) The method of (14), further comprising the step:
  placing at least one of said two or more three-dimensional portions in another of said two or more three-dimensional portions after the step of heating the primary coil wound and after the step removing the primary coil from the mandrel and before placing the primary coil into a lumen of a mold.

(16) An in vivo indwelling member obtained by a method, the method comprising:
  providing a wire;
  winding the wire around a linear mandrel and removing the linear mandrel therefrom so that the wire is formed into a primary coil;
  inserting a core wire into a lumen of the primary coil;
  winding the primary coil around a mandrel having a winding portion so that the primary coil is formed into an intermediate shape, the intermediate shape two or more three-dimensional portions, each of the three-dimensional portions being formed by continuously providing at least four of the shape parts over four planes, all of the four planes having normal directions perpendicular to a predetermined common axis direction, each of the at least four shape parts being formed in any of respective planes of a virtual cylindrical body having a shape of a quadrangle as seen from the common axis surrounded by the four planes,
  heating the primary coil wound on the mandrel at 400° C. or higher for 15 minutes or longer;
  removing the primary coil from the mandrel;
  placing the primary coil into a lumen of a mold; and
  heating the primary coil in the lumen of the mold at 400° C. or higher for 15 minutes or longer at 400° C. or higher for 15 minutes or longer to form a secondary shape.

(17) The in vivo indwelling member of (16), wherein the method further comprises the step:
  placing at least one of said two or more three-dimensional portions in another of said two or more three-dimensional portions after the step of heating the primary coil wound and after the step removing the primary coil from the mandrel and before placing the primary coil into a lumen of a mold.

Advantageous Effects of Invention

The in vivo indwelling member according to the present invention, which is configured as described above, includes two or more three-dimensional portions, each of the three-dimensional portions being formed by continuously providing at least four of the curved parts over four planes, all of the four planes having normal directions perpendicular to a predetermined common axis direction, each of the at least four curved parts being formed in any of respective planes of a virtual cylindrical body having a shape of a quadrangle as seen from the common axis surrounded by the four planes. Accordingly, in the three-dimensional portions as described above, the curved parts arranged on the four planes of the cylindrical body along the aneurysm wall are adhered to an inner wall of the aneurysm or the like so as to expand outward according to a shape of the inner wall of the aneurysm. The three-dimensional portions can form a frame with high adhesion along the inner wall. Moreover, two or more of the three-dimensional portions can be sequentially developed so as to form multiple frames, whereby the adhesion is enhanced, and an indwelling density is also increased.

That is, in the conventionally proposed in vivo indwelling members, the three-dimensional shapes have such strong shape retention that loop-shaped parts interfere with each other. Meanwhile, in the present invention, the curved parts of the four planes of the virtual cylindrical body have a flexible three-dimensional shape that easily spreads outward and is developed independently without causing interference thereamong. Therefore, as described above, the adhesion to the inner wall of the aneurysm or the like is enhanced, the indwelling density is also improved in such a manner that such three-dimensional portions are sequentially developed, the curved parts hardly get caught with each other during the operation, and good operability is maintained.

In addition, in the present invention, in a structure in which the three-dimensional portions are set so that the three-dimensional portion having a relatively small area of the quadrangle as seen from the common axes of the virtual cylindrical bodies is disposed on a tip end side of the primary coil, and that the three-dimensional portion having a relatively large area of the quadrangle as seen from the common axes of the virtual cylindrical bodies is disposed on a base end side of the primary coil, the small three-dimensional portion that previously forms the frame is pressed toward the inner wall side in such a direction of further spreading by the large three-dimensional portion pushed out later. In this way, the adhesion of the in vivo indwelling member is further strengthened, a strong frame along the inner wall is formed, thus making it possible to more reliably prevent the falling off.

Here, the length of the primary coil that constitutes the three-dimensional portion excluding the largest three-dimensional portion, that is, the three-dimensional portion previously pushed out into the aneurysm or the like can also be set to a length of 25% or more and 50% or less of the overall length of the primary coil. In this way, there can be maintained a sufficient volume to enable the following actions to function, the actions are: to form a sufficient amount of the frame by the three-dimensional portion pushed out previously; and in addition, to make it possible to form a frame excellent in adhesion by further spreading the frame to the inner wall side as described above also with regard to the largest three-dimensional portion pushed out last.

Moreover, such an anchor portion formed of at least one of the curved parts can also be provided in a region of the primary coil, the region leading to a tip of the primary coil more on a tip end side than the smallest three-dimensional portion, and a length of the primary coil that constitutes the anchor portion can also be set to a length of less than 15% of the overall length of the primary coil. In this way, the anchor portion is stably held on the inner wall of the aneurysm or the like when the anchor portion is first pushed out into the aneurysm or the like, it is possible to more smoothly spread the three-dimensional portion, which is to be pushed out thereafter, and to smoothly adhere the three-dimensional portion to the inner wall, and the adhesion to the inner wall and the indwelling density, which are mentioned above, can be improved, and the operability is also improved. When the anchor portion is longer than 15%, the retention stability with respect to the inner wall is reduced, and a function thereof as an anchor decreases.

Meanwhile, such a structure, in which the three-dimensional portions are set, in order from a tip end side toward a base end side of the primary coil, so that the three-dimensional portion having a relatively large area of the quadrangle as seen from the common axes of the virtual cylindrical bodies is disposed on the tip end side, and that the three-dimensional portion having a relatively small area of the quadrangle as seen from the common axes of the virtual cylindrical bodies is disposed on the base end side, is suitable for a relatively small aneurysm. A strong frame is formed by the large three-dimensional portion that entered previously. The smaller three-dimensional portion pushed out later serves as a filling (filler). This reduces a number of steps of a method using the coil, and can reduce burdens on a patient and a doctor.

Here, the length of the primary coil that constitutes the three-dimensional portion excluding the smallest three-dimensional portion can also be set to a length of 25% or more and 70% or less of the overall length of the primary coil. In this way, a sufficient amount of the frame is formed by the three-dimensional portion pushed out previously, and in addition, the smallest three-dimensional portion pushed out last also serves as the filling sufficiently as described above.

Moreover, such an anchor portion formed of at least one of the curved parts can also be provided in a region of the primary coil, the region leading to a tip of the primary coil more on a tip end side than the largest three-dimensional portion, and a length of the primary coil that constitutes the anchor portion can also be set to a length of less than 15% of the overall length of the primary coil. In this way, as described above, the anchor portion is stably held on the inner wall of the aneurysm or the like when the anchor portion is first pushed out into the aneurysm or the like, it is possible to more smoothly spread the three-dimensional portion, which is to be pushed out thereafter, and to smoothly adhere the three-dimensional portion to the inner wall, and the adhesion to the inner wall and the indwelling density, which are mentioned above, can be improved, and the operability is also improved. When the anchor portion is longer than 15%, the retention stability with respect to the inner wall is reduced, and a function thereof as an anchor decreases.

Moreover, with regard to a ratio of the areas of the three-dimensional portion having a relatively small area of the quadrangle as seen from the common axis of the virtual cylindrical body and of the three-dimensional portion having a next large area of the quadrangle as seen from the common axis of the virtual cylindrical body, the ratio can also be set so that the area of the large three-dimensional portion is 1.1 times or more and 2.3 times or less the area of the small three-dimensional portion. In this way, the frame previously formed by the relatively small three-dimensional portion is pushed and spread toward the inner wall side by the next large three-dimensional portion, and such a firm frame along the inner wall of the aneurysm or the like is reliably formed. On the contrary, the next small three-dimensional portion is loaded inside the frame previously formed by the relatively large three-dimensional portion, and can be caused to sufficiently function as the filling.

Moreover, with regard to a ratio of shortest side that constitutes the quadrangle of the three-dimensional portion having a relatively small area of the quadrangle as seen from the common axis of the virtual cylindrical body and of a shortest side that constitutes the quadrangle of the three-dimensional portion having a next large area of the quadrangle as seen from the common axis of the virtual cylindrical body, the ratio can also be set so that the length of the large three-dimensional portion is 1.05 times or more and 1.5 times or less the length of the small three-dimensional portion. In this way, likewise, the frame previously formed by the relatively small three-dimensional portion is pushed and spread toward the inner wall side by the next large three-dimensional portion, and such a firm frame along the inner wall of the aneurysm or the like is reliably formed. On the contrary, the next small three-dimensional portion is loaded inside the frame previously formed by the relatively large three-dimensional portion, and can be caused to sufficiently function as the filling.

Moreover, the quadrangles as seen from the common axes of the virtual cylindrical bodies can also be squares. The three-dimensional portions as described above spread so as to expand outward more uniformly according to the shape of the inner wall surface of the aneurysm or the like, a stable frame with high adhesion can be formed along the inner wall, and the indwelling density can also be further increased.

In addition, the four or more curved parts can also be formed in any of the planes which are the squares of each of the virtual cylindrical bodies. In this way, the three-dimensional portions as described above spread so as to expand outward more uniformly, a more stable frame with high adhesion can be formed along the inner wall, and the indwelling density can also be further increased.

Moreover, another solid can be disposed inside one of the solids, and the common axes of the respective solids can be parallel to each other. In addition, the three-dimensional portion smaller than the largest three-dimensional portion can be disposed inside the largest three-dimensional portion, and the common axes of the respective three-dimensional portions can be parallel to each other. In this way, when pushed out into the aneurysm or the like, such a frame which has been previously formed by the relatively small three-dimensional portion can be further pressed and expanded to the inner wall side more reliably by the largest three-dimensional portion, and the above-described adhesion and indwelling density can be further enhanced. Moreover, on the contrary, the relatively small three-dimensional portion is loaded inside the frame previously formed by the relatively large three-dimensional portion, and can be caused to sufficiently function as the filling.

Moreover, an in vivo indwelling member placement device according to the present invention includes: an in vivo indwelling member placement wire; the in vivo indwelling member according to the present invention described above; and a cuttable coupling member that couples the wire and the in vivo indwelling member to each other. Therefore, in accordance with the in vivo indwelling member placement device, the in vivo indwelling member placement wire can be removed by cutting the coupling member without adversely affecting the frame structure of the indwelled coil along the inner wall, the adhesion thereof, the effect as a filling, and the like.

Moreover, the coupling member can also be formed of a thermally soluble material. In this way, the above-described cutting operation can be performed reliably and smoothly, and the wire removal can be completed.

DESCRIPTION OF EMBODIMENTS

Figure 1:
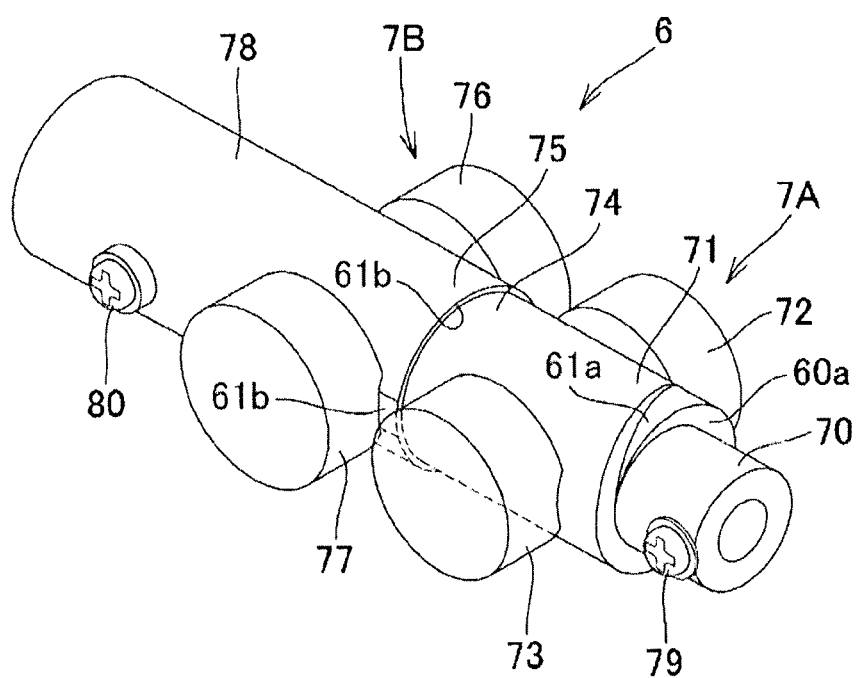
FIG. 1 is a perspective view showing a mandrel for forming an intermediate shape of an in vivo indwelling member according to a representative embodiment of the present invention.

Next, embodiments of the present invention will be described in detail with reference to the accompanying drawings. A shape of an in vivo indwelling member, which is defined in the claims of the present invention, is a shape imparted in such a manner that the in vivo indwelling member is wound around a mandrel. Note that shapes and intermediate shapes of secondary coils, which are shown in the drawings and are not accompanied by the mandrel, are each drawn assuming a state in which a reinforcement core material (core wire) is inserted into a lumen of a primary coil. These shapes and intermediate shapes are shown to help understanding thereof.

Figure 9A:
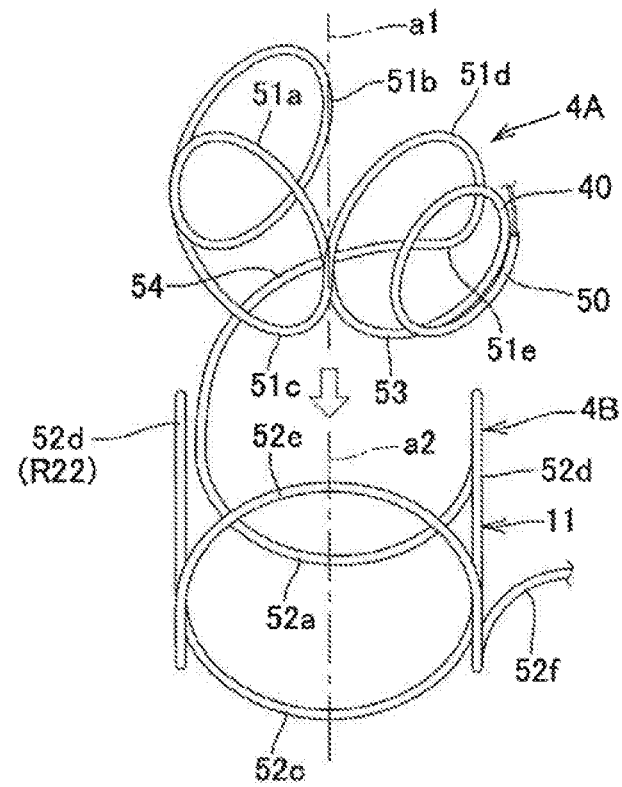
FIG. 9(a) is an explanatory diagram showing a state in which a middle solid and an anchor portion of the intermediate-shape coil are disposed inside a large solid.
Figure 9B:
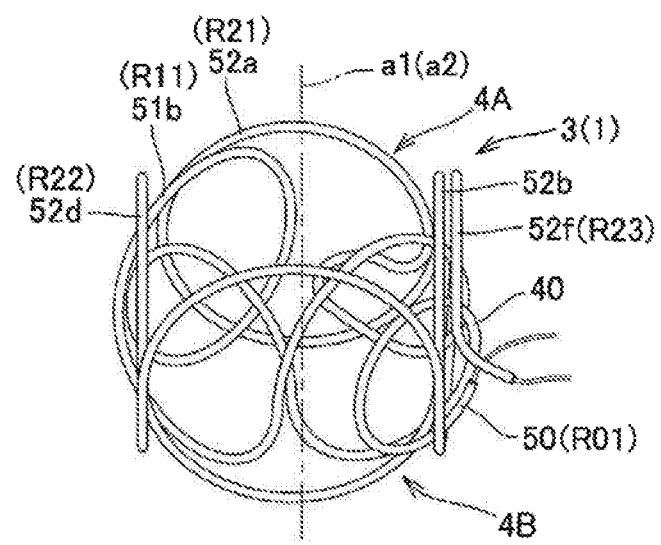
FIG. 9(b) is a perspective view showing a shape of a secondary coil (in vivo indwelling member) having the above disposition.

As shown in FIG. 9(b), in an in vivo indwelling member 1 according to the present invention, shapes of two or more three-dimensional portions (middle solid 4A, large solid 4B) are provided in a primary coil 11. As shown in schematic views in FIG. 11, each three-dimensional portion is formed by continuously providing at least four curved parts (51a to 51e/52a to 52f) over four planes (F1 to F4/F5 to F8). Normal directions of the four planes (F1 to F4/F5 to F8) each have a relationship perpendicular to a predetermined common axis (a1/a2) direction. Each of the at least four curved parts (51a to 51e/52a to 52f) is formed on each of the planes (F1 to F4/F5 to F8) of a quadrangular virtual cylindrical body (C1/C2) as seen from the common axis (a1/a2) surrounded by the four planes.

In these three-dimensional portions (middle solid 4A, large solid 4B), the curved parts arranged on the four planes of the cylindrical body are adhered to an inner wall of an aneurysm or the like so as to expand outward according to a shape of the inner wall of the aneurysm. The three-dimensional portions can form a frame with high adhesion along the inner wall. The three-dimensional portions as described above can be sequentially developed so as to form multiple frames, whereby the adhesion is enhanced, and an indwelling density is also increased. In the following embodiment, after an intermediate-shape coil 2 having the middle solid 4A and the large solid 4B is formed, a shape is further imparted so that the middle solid 4A is disposed inside the large solid 4B. However, this process may be omitted, and the intermediate-shape coil 2 may be used as a final secondary coil instead of an intermediate one, and this final secondary coil may be used as the in vivo indwelling member. In this embodiment, two three-dimensional bodies which are the middle solid and the large solid are formed in the in vivo indwelling member, but three or more solids may be formed.

Hereinafter, a detailed description will be made of a procedure of forming the intermediate-shape coil 2 formed by using a mandrel 6 and further forming the secondary coil from the intermediate-shape coil 2.

Figure 5A:
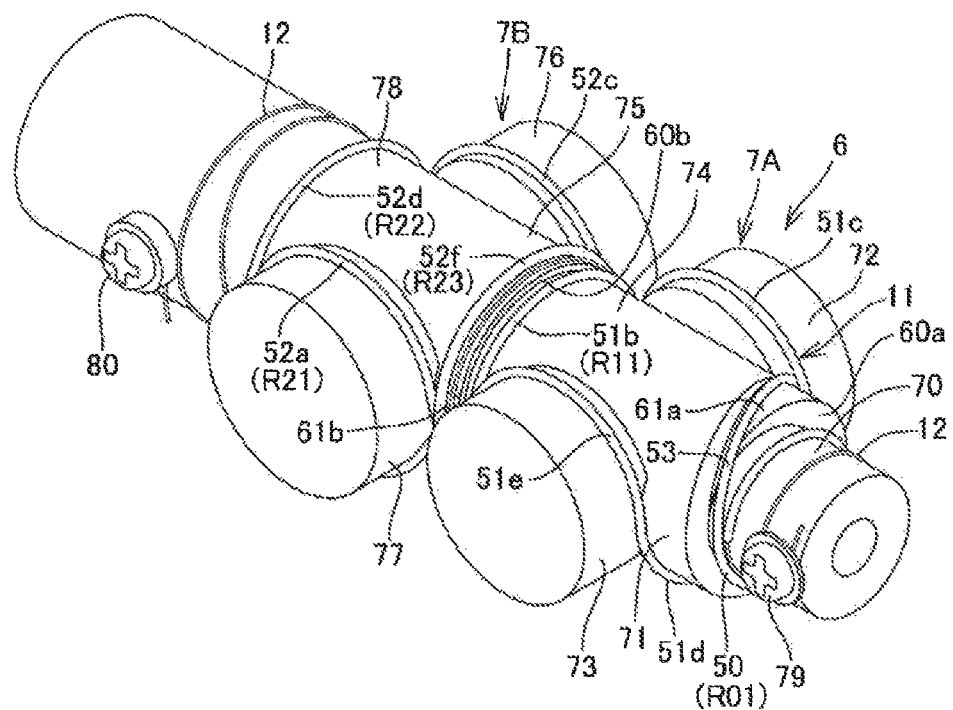
FIG. 5(a) is a perspective view showing a state in which a primary coil is wound around the mandrel.
Figure 5B:
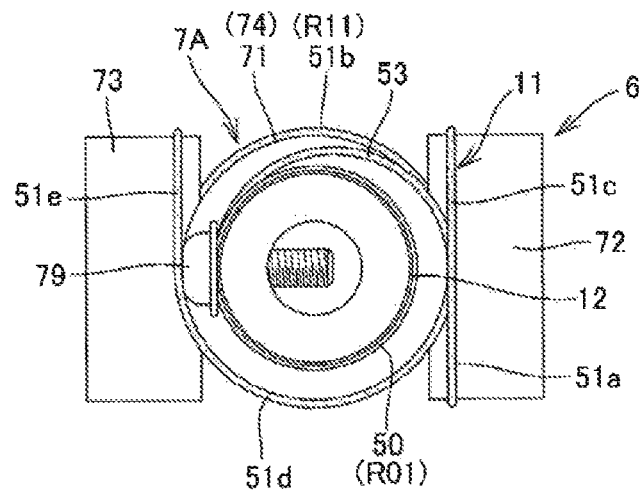
FIG. 5(b) is a partial front view showing a state in which the primary coil is wound around the mandrel.
Figure 6A:
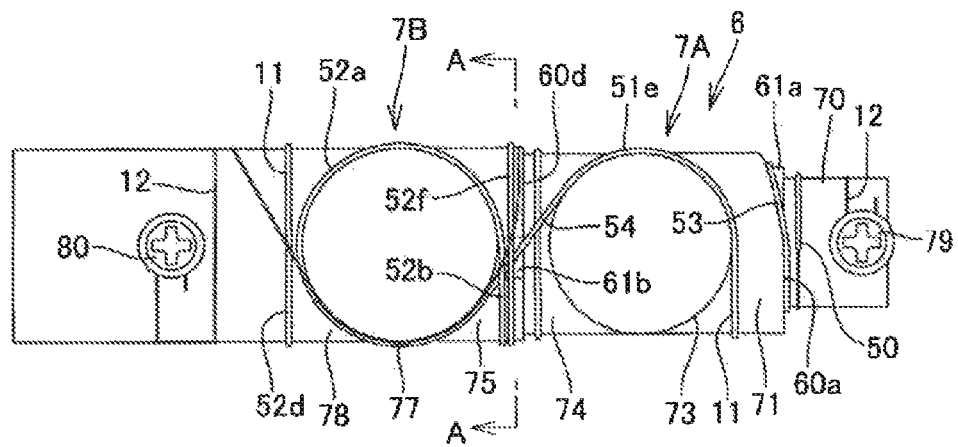
FIG. 6(a) is a perspective view showing a state in which the primary coil is wound around the mandrel.
Figure 6B:
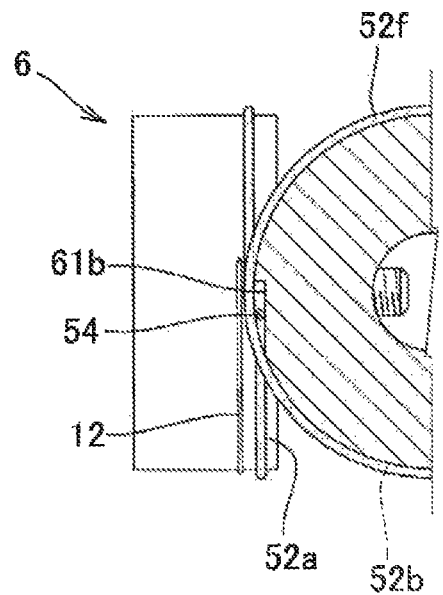
FIG. 6(b) is a partial cross-sectional view of the state, taken along a line A-A of FIG. 6(a).
Figure 7:
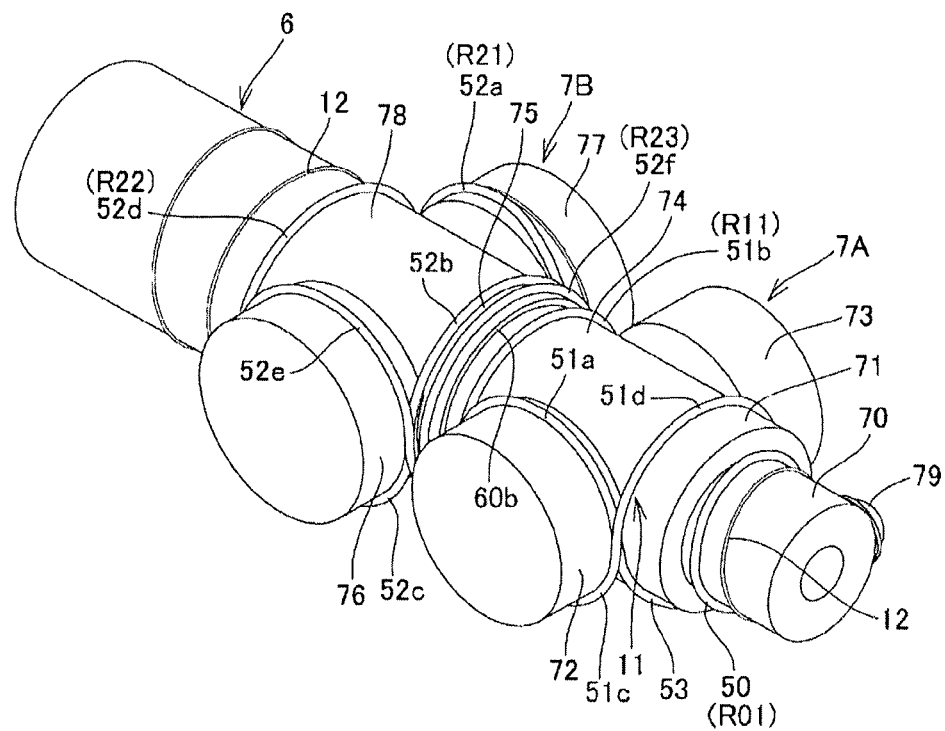
FIG. 7 is a perspective view of a state in which the primary coil is wound around the mandrel as seen from a lower surface side thereof.

As shown in FIGS. 5 to 7, the mandrel 6 for manufacturing the in vivo indwelling member according to the present invention is used for winding a primary coil 11 therearound to form a secondary shape (in this example, an intermediate shape before the secondary shape) of the in vivo indwelling member. The mandrel for manufacturing the in vivo indwelling member of the present invention is not limited to this, and can be appropriately selected according to a configuration of the in vivo indwelling member.

In the following description, a side of the mandrel 6, which includes a winding portion 70, will be referred to as "one end side", and the other side of the mandrel 6, which includes an aggregate 7B, will be referred to as "the other end side". A side of the primary coil, which is previously wound around the mandrel 6, will be referred to as "front end side", and a side of the primary coil, which is wound around the mandrel 6 later, will be referred to as "rear end side". A distal side of the primary coil or a secondary coil, which is previously pushed out to the aneurysm or the like will be referred to as "tip end side", and a proximal side of the primary coil or the secondary coil, which is pushed out later, will be referred to as "base end side". Here, the secondary coil is obtained by imparting a secondary shape to the primary coil, and is used as the in vivo indwelling member.

In the following example, a description will be made of an example in which an anchor portion, a middle solid, and a large solid are formed by being wound in this order from the front end side of the primary coil, and the front end side is configured as the tip end side which is previously pushed out to the aneurysm or the like. However, as a matter of course, the large solid, the middle solid, and the anchor portion can be formed by being wound in this order from the front end side, and the front end side can be configured as the base end side. Moreover, the in vivo indwelling member of the present invention can also be configured not to include the anchor portion.

Figure 10A:
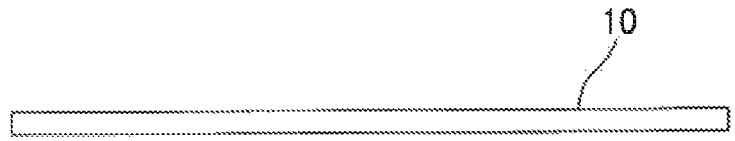
FIGS. 10(a) to 10(d) are explanatory diagrams for explaining a procedure for manufacturing the primary coil.
Figure 10B:
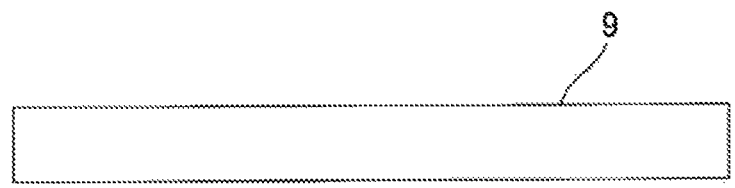
Figure 10C:
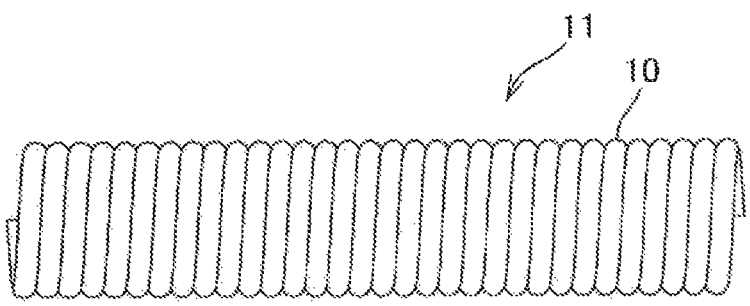
Figure 10D:
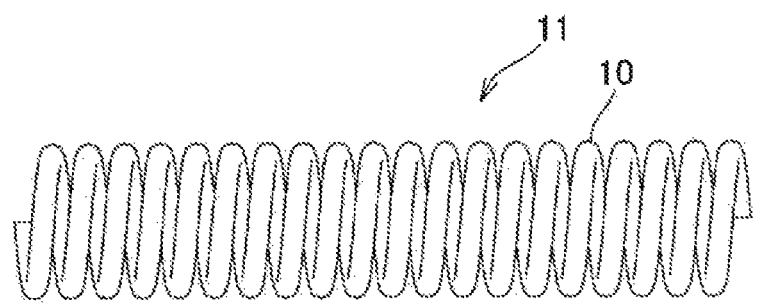

As the primary coil 11, those which are conventionally known and are used in the in vivo indwelling member can be widely applied. The primary coil 11 of this example is a coil given such a spiral primary shape as shown in FIG. 10(c) or FIG. 10(d) in such a manner that a wire 10, which is a single or stranded wire as shown in FIG. 10(a), is wound around a mandrel 9 or the like, which is a linear rod-shaped member as shown in FIG. 10(b). Loops of such spiral winding of the primary coil may be in contact with one another as shown in FIG. 10(c), or may not be in contact with one another as shown in FIG. 10(d). The primary coil may be formed only as in FIG. 10(c) or only as in FIG. 10(d), or may be a combination of FIGS. 10(c) and 10(d). Moreover, the single primary coil may include a plurality of portions having shapes shown in FIG. 10(c) and a plurality of portions having shapes shown in FIG. 10(d).

A material of the wire 10 is not particularly limited, and examples thereof include a simple substance such as platinum, tungsten, iridium, tantalum, gold, and stainless steel, or an alloy formed by combining at least two of these. These materials are radiopaque materials.

In general, diameter of the wire 10 is preferably 10 to 150 μm (0.01 mm to 0.15 mm) and more preferably 25 to 135 μm (0.025 mm to 0.135 mm). A diameter of the wire 10 can be selected as appropriate depending on the purpose of use or the like without particular limitation. For example, in the case of using the wire 10 for treatment of aneurysm obliteration, the diameter is preferably 0.010 mm or more to 0.200 mm or less, more preferably 0.030 mm or more to 0.100 mm or less. In addition, an outer diameter of the primary coil 11 is preferably 150 to 500 μm (0.150 mm to 0.500 mm) and more preferably 200 to 460 μm (0.200 mm to 0.460 mm). An outer diameter or width of the primary coil 11 can be selected as appropriate depending on the purpose of use or the like without particular limitation. For example, in the case of using the primary coil 11 for the treatment of the aneurysm obliteration, the outer diameter or the width is preferably 0.100 mm or more to 0.500 mm or less. In addition, an overall length of the primary coil 11 can also be selected as appropriate depending on the purpose of use or the like without particular limitation. For example, in the case of using the primary coil 11 for the treatment of the aneurysm obliteration, the overall length is preferably 10 mm or more to 1000 mm or less.

The shape formed by winding the primary coil 11 around the mandrel 6 of this example is not a final secondary shape but a shape in the course of reaching the final secondary shape. That is, the mandrel 6 of this example forms the intermediate-shape coil 2. The final secondary shape of the in vivo indwelling member (in vivo indwelling member 1 which is a secondary coil 3) is a shape shown in FIG. 9(b) obtained by further arranging the middle solid 4A and an anchor portion 40 inside the large solid 4B as described later, followed by heating.

In the mandrel of this example, stepped portions 60a and 60b are provided at predetermined positions through which the primary coil 11 passes by winding, and further, notch grooves 61a and 61b which receive the primary coil 11 are provided on the stepped portions 60a and 60b. However, other embodiments of the present invention are not limited to this. The notch grooves may or may not be provided. In this example, as will be described later, as the notch grooves provided on the mandrel 6, there are formed: the sloped notch groove 61a formed on the stepped portion 60a between an aggregate 7A for molding the middle solid 4A of the intermediate-shape coil and the winding portion 70 for molding the anchor portion 40; and a rectangular notch groove 61b formed on the stepped portion 60b between the aggregate 7B for molding the large solid 4B and the aggregate 7A for molding the middle solid 4A.

Figure 2A:
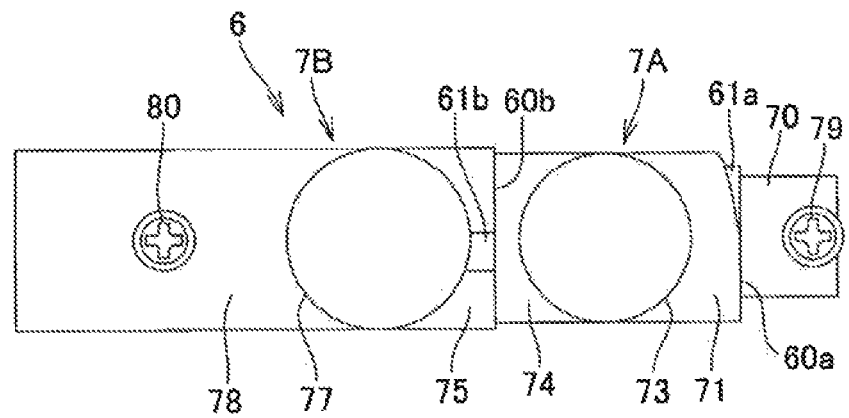
FIGS. 2(a) and 2(b) are side views of the mandrel.
Figure 2B:
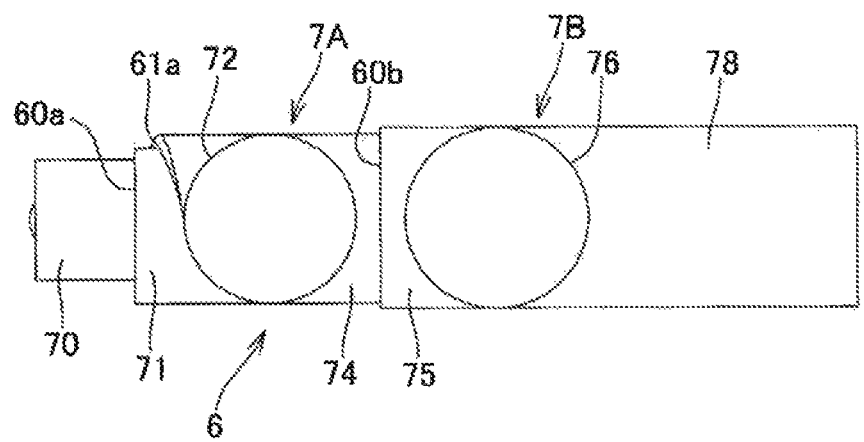
Figure 2C:
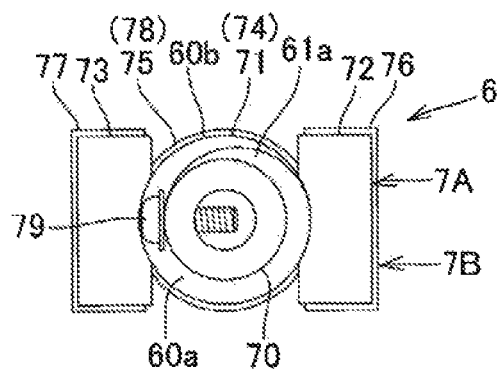
FIG. 2(c) is a front view of the mandrel as seen from one end side (side on which an anchor portion is formed).
Figure 3A:
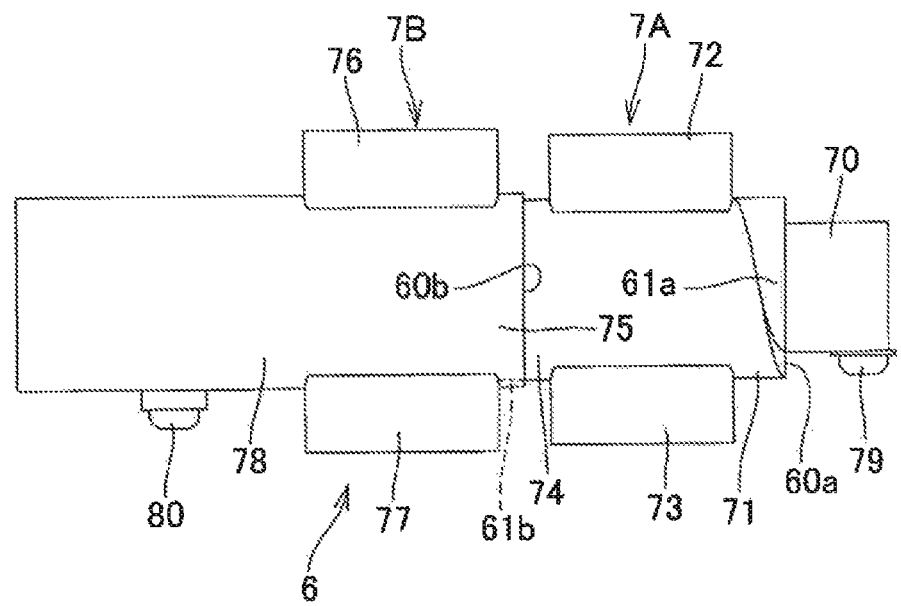
FIG. 3(a) is a front view of the mandrel as seen from above.
Figure 3B:
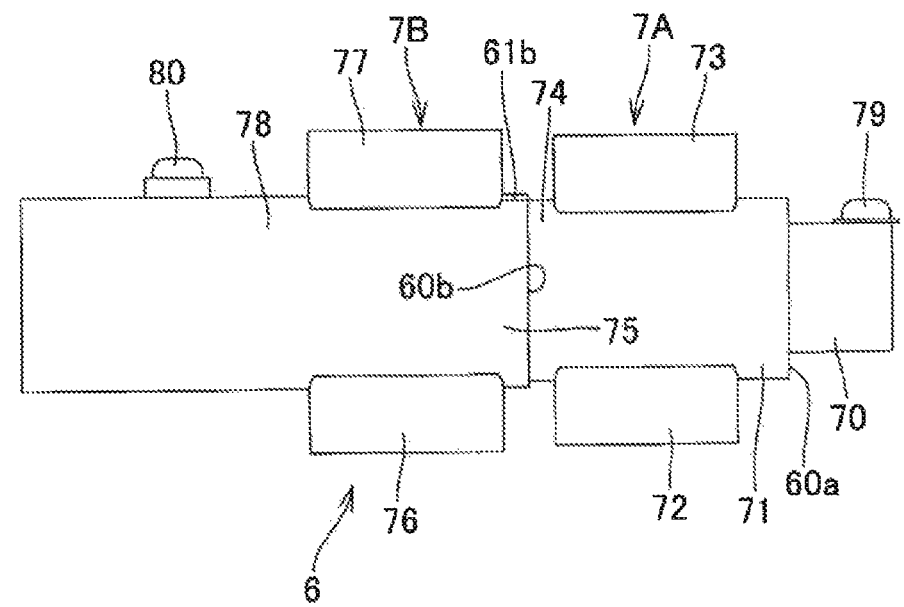
FIG. 3(b) is a bottom view of the mandrel as seen from below.

As shown in FIGS. 1 to 3, the mandrel 6 includes a plurality of winding portions 70 to 78, each of which has an outer circumferential surface around which the primary coil 11 is wound by one or more turns or less than one turn. Moreover, the stepped portions 60a and 60b are formed, respectively, between a winding portion in which a circumferential length of an outer circumferential surface is relatively long and a winding portion in which a circumferential length of an outer circumferential surface is relatively short, which are continuously provided coaxially with each other, in this example, between the winding portion 71 and the winding portion 70, and between the winding portion 75 and the winding portion 74.

In this example, the winding portions 70 to 78 are formed of rod-shaped portions having circular cross sections as seen from axial directions of the respective winding portions, but the winding portions are not limited to such a circular shape, and for example, a rounded polygonal shape, an ellipsoidal shape, and the like are also preferable. The winding portions 70 to 78 may be hollow cylinders rather than rods of which cores are dense solid. Outer diameters of the respective winding portions 70 to 78 circular in cross section are preferably 1 mm or more and 30 mm or less when the in vivo indwelling member is used for the treatment of the aneurysm obliteration. This is because the outer diameters of the winding portions directly determine sizes of the loop-shaped parts in the secondary coil and curvatures or curved degrees of the respective curved parts, and it is preferable that these values result in the shape that adheres to the inner wall of an aneurysm having an inner diameter of 1 to 30 mm.

More specifically, the mandrel 6 includes two aggregates, which are the aggregate 7A including the winding portions 71 to 74 in which circumferential lengths of outer circumferential surfaces are substantially the same (lengths of the outer circumferences are substantially the same if the cross-sections are circular as in this example), and the aggregate 7B including the winding portions 75 to 78 in which circumferential lengths of outer circumferential surfaces are substantially the same. The circumferential length of the respective winding portions 71 to 74 of the aggregate 7A is shorter than the circumferential length of the respective winding portions 75 to 78 of the aggregate 7B, and these aggregates 7B and 7A are integrated with each other in a state in which the single winding portion 75 of the aggregate 7B and the single winding portion 74 of the aggregate 7A are continuously provided coaxially with each other. The circumferential length of the respective winding portions 75 to 78 of the aggregate 7B is preferably set to 1.05 times or more to 1.5 times or less the circumferential length of the respective winding portions 71 to 74 of the aggregate 7A, more preferably, 1.1 times or more to 1.2 times or less the circumferential length. The stepped portion 60b is formed between the winding portions 74 and 75 provided continuously with each other.

Among the four winding portions 71 to 74 which constitute the aggregate 7A, the winding portions 71 and 74 are front and rear parts of a columnar portion integrally formed coaxially, and the winding portions 72 and 73 are protruded leftward and rightward from midway positions of the columnar portion while taking, as a common axis, an axis perpendicular to an axis of the cylindrical portion. In this way, axial directions of the winding portions 71 to 74 become four directions shifted from one another by 90 degrees on the same plane, and the winding portions 71 to 74 are arranged in an annular shape. Likewise, the four winding portions 75 to 78 which constitute the aggregate 7B are also arranged in an annular shape.

In this example, the respective central axes of the winding portions 71 to 74 of the aggregate 7A and the respective central axes of the winding portions 75 to 78 of the aggregate 7B are all arranged on the same plane, and the common axis of the winding portions 72 and 73 of the aggregate 7A and the common axis of the winding portions 76 and 77 of the aggregate 7B are arranged so as to be parallel to each other. Moreover, as seen from the aggregate 7A, on an opposite side to the aggregate 7B on the same axis, the winding portion 70 having a circumferential length shorter than the circumferential length of the winding portions 71 to 74 of the aggregate 7A is provided coaxially with the winding portion 71. The stepped portion 60a is also formed between these coaxial winding portions 70 and 71.

Figure 4:
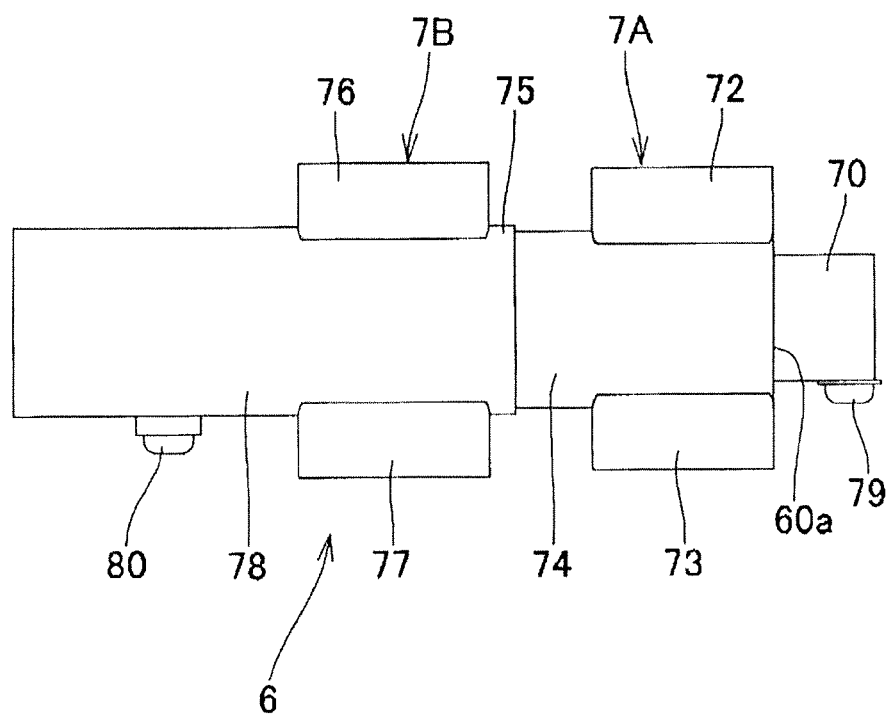
FIG. 4 is a front view showing a modified example of the mandrel as seen from above.

On these stepped portions 60a and 60b, the notch grooves 61a and 61b which receive the primary coil 11 when passing the primary coil 11 therethrough are provided. The notch groove 61a is a portion where an anchor portion forming part including only the single winding portion 70 and the aggregate 7A that forms the middle solid 4A are provided continuously with each other, and since the primary coil 11 extends substantially in the circumferential direction between the winding portion 70 and the winding portion 71, a part between the winding portion 70 and the winding portion 71 is formed of a slope-shaped notch. The notch groove 61b is a portion where the middle solid 4A and the large solid 4B are provided continuously with each other. According to a winding method of this example, since the primary coil 11 extends in a direction closer to the axial direction than to the circumferential direction of the winding portions 74 and 75, the notch groove 61b is formed of a rectangular notch, but the notch groove 61b is not at all limited to this shape. Moreover, as mentioned above, the mandrel 6 may be, as shown in FIG. 4, a mandrel in which the notch grooves (61a, 61b) and the winding portion 71 are omitted.

Furthermore, as will be described later, the anchor portion 40 of this example is not a three-dimensional portion having four curved parts such as the middle solid 4A and the large solid 4B, but a portion formed of one curved part 50 and a spiral part 53. Therefore, only one winding portion 70 of the mandrel 6 for forming the anchor portion 40 is provided, and an aggregate including two or more winding portions having different axial directions as described above is not formed. However, the winding portion 70 is not limited to such a configuration. It is a matter of course that the winding portion of the mandrel for forming the anchor portion can be formed as an aggregate including two or more winding portions, and the anchor portion can be configured as a three-dimensional portion.

Moreover, in this example, the two aggregates 7A and 7B are formed of the winding portions 70 to 78, but a larger number of aggregates may be provided continuously therewith by increasing the winding portions. In this case, in a part of the aggregates of the plurality of aggregates, circumferential lengths of the winding portions thereof may be substantially equal to one another. In this case, a plurality of three-dimensional shapes having the same size are formed.

Further, in this example, the winding portion 70 that forms the anchor portion and the above-described aggregates 7A and 7B are formed in order from the one end side, but it is of course possible to change this order of the arrangement. In this case, forms of the stepped portions and passing positions of the primary coil at the stepped portions when winding the primary coil also change, but it is preferable to form the notch grooves appropriately at the passing positions in the same manner as this example. Specific circumferential lengths of the outer circumferential surfaces of the respective winding portions 70 to 78 are selectable as appropriate according to the purpose of use of the in vivo indwelling member and the shapes and structures of the middle solid 4A, the large solid 4B, and the anchor portion 40, which are to be formed.

Figure 8:
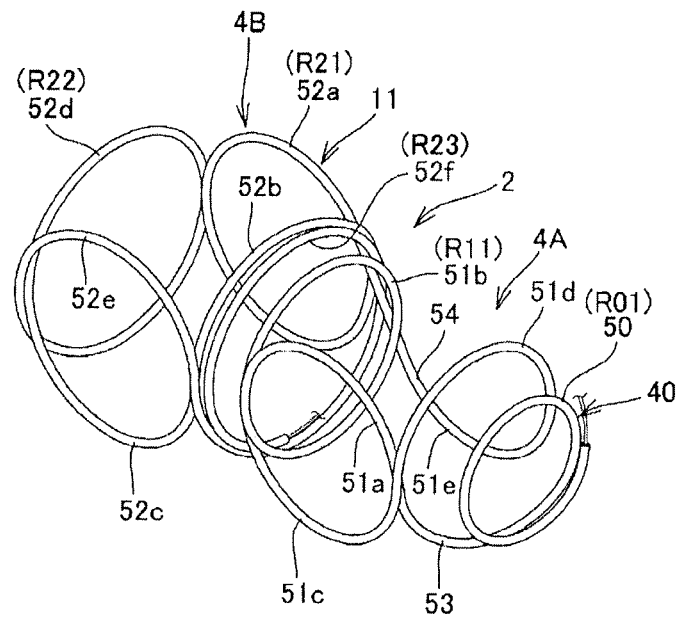
FIG. 8 is a perspective view showing a shape of an intermediate-shape coil formed by the mandrel.

As shown in FIG. 8, the intermediate shape formed by winding the primary coil 11 around such a mandrel 6 as described above has the above-mentioned two or more three-dimensional portions (middle solid 4A, large solid 4B). Note that the shape of the secondary coil and the intermediate shape, which are shown in the drawings and are not accompanied by the mandrel, illustrate such a state in which the reinforcement core material (core wire) is inserted into the lumen of the primary coil. Specifically, the curved parts 50, 51a to 51e, and 52a to 52f in the primary coil 11, which extend continuously and curvedly on substantially the same plane, are formed on two or more planes by the respective winding portions of the mandrel 6 described above, and form a three-dimensional shape. Note that, as long as the primary coil 11 is roughly along substantially the same plane, the phrase "on substantially the same plane" includes a case where it can be regarded that these parts are on substantially the same plane although are somewhat deviated from the plane from a strict viewpoint in such a case where the primary coil 11 is curved in a loop shape or a spiral shape and these spiral shapes overlap each other double or triple. In FIG. 8, the curved parts 51a and 51c are combined with each other to form an annular ring, and such a constituent portion, which is formed by combining a plurality of curved parts, each of which extends less than one turn and does not form a loop, with each other to form the annular ring, is referred to as an annular ring constituent portion. The intermediate shape includes such an annular ring constituent portion, whereby a bias of the coil in the aneurysm is reduced, and the adhesion of the coil to the inner wall of the aneurysm is improved.

Figure 11A:
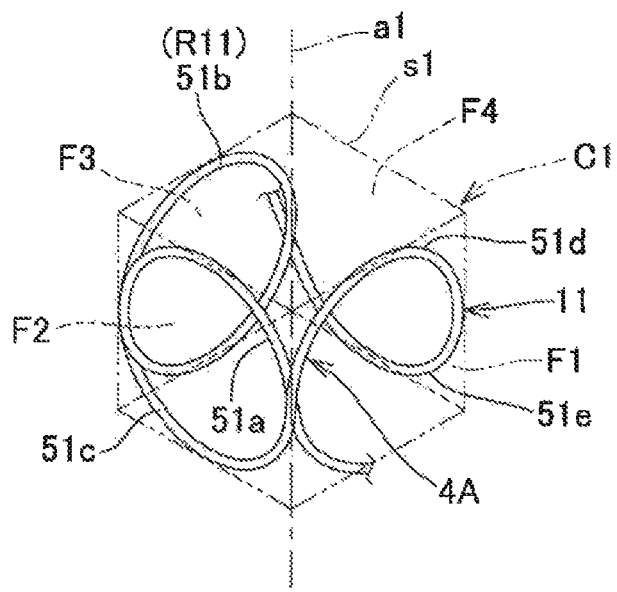
FIGS. 11(a) and 11(b) are explanatory diagrams for explaining configurations of the middle and large solids in the intermediate-shape coil and the secondary coil by using a virtual cylindrical body.
Figure 11B:
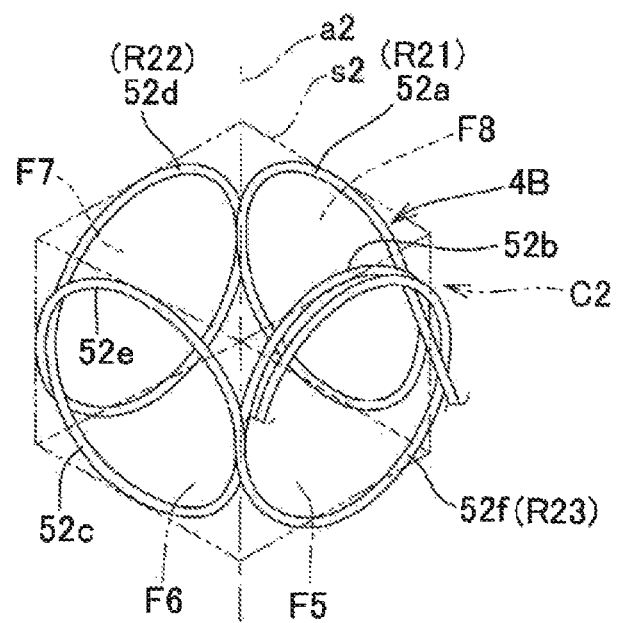

In this example, two three-dimensional portions, i.e., the three-dimensional portion (middle solid 4A) formed by continuously providing at least four curved parts 51a to 51e over four planes; and the three-dimensional portion (large solid 4B) formed by continuously providing at least four curved parts 52a to 52f over four planes, are formed by the aggregates 7A and 7B of the mandrel 6, respectively. As shown in FIGS. 11(a) and 11(b), with regard to the four planes of each of the three-dimensional portions, all of the normal directions thereof are perpendicular to the predetermined common axis a1/a2 direction. Each of the curved parts (51a to 51e, 52a to 52f) which constitute the respective three-dimensional portions (middle solid 4A, large solid 4B) is formed in any of the respective planes (F1 to F4, F5 to F8) of the quadrangular virtual cylindrical bodies C1 and C2 as seen from the common axes surrounded by the four planes.

As described above, the respective three-dimensional portions (middle solid 4A/large solid 4B) are formed as three-dimensional portions, in which the curved parts 51a to 51e/52a to 52f of the primary coil are formed on the four planes F1 to F4 and four planes F5 to F8 of the virtual cylindrical bodies C1/C2, respectively, and no curved parts are present on upper and lower surfaces in the axial direction of the virtual cylindrical bodies. Therefore, when pushed out into the aneurysm or the like, the primary coil spreads into the three-dimensional shape without being confined. At the same time, the three-dimensional portions do not have too strong shape retention, and is deformable relatively flexibly according to the shape of the inner wall of the aneurysm or the like, thus making it possible to form a frame with high adhesion along the inner wall. Moreover, the curved parts hardly get caught with each other when the three-dimensional portions are pushed out and returned, and good operability is maintained.

These three-dimensional portions are formed in the intermediate-shape coil, and in this example, are further processed into a secondary shape in which the anchor portion 40 and the middle solid 4A are arranged inside the large solid 4B of the intermediate-shape coil. However, as in the previous description, these middle solid 4A and large solid 4B are developed in order inside the aneurysm or the like.

These three-dimensional portions are formed so that, from the front end side of the primary coil 11, which is previously wound, toward a rear end side thereof, a three-dimensional portion having a relatively small area of a quadrangle seen from the common axis of the virtual cylindrical body, i.e., the middle solid 4A in this example, and a three-dimensional portion having a relatively large area of the quadrangle, i.e., the large solid 4B in this example, are arranged in this order, so that the large solid 4B is placed on the rear end side. In this example, two three-dimensional portions, which are the middle solid 4A and the large solid 4B, are formed in order as described above.

The reason why the portion denoted by 4A is referred to as the "middle solid" is as follows. Incidentally, there is not another three-dimensional portion which has a smaller area of the quadrangle and is referred to as a "small solid", and the existence of the "small solid" is not the reason. The reason is that the middle solid 4A has a larger three-dimensional shape than the anchor portion 40 since, although the anchor portion 40 is not a three-dimensional portion surrounded by such four planes, the anchor portion 40 has a three-dimensional shape including the loop-shaped curved part 50 (loop-shaped part R01) smaller than a loop-shaped part R11 of the middle solid 4A, which is the curved part 51b circled in a 360-degree loop shape. As mentioned above, a plurality of the three-dimensional shapes having the same size may be formed, or a plurality of the middle solids may be formed.

Then, the primary coil 11 is pushed out into the aneurysm while placing, on the tip end side, the front end side thereof where the relatively small three-dimensional portion (middle solid 4A) is formed, and placing, on the base end side, the rear end side thereof where the relatively large three-dimensional portion (large solid 4B) is formed. Then, the small three-dimensional portion (middle solid 4A), which is developed previously and forms a frame on the wall surface of the aneurysm, is pressed toward the inner wall side in a further expanding direction by the larger three-dimensional portion (large solid 4B) which is pushed out later into the aneurysm. In this way, the adhesion of the primary coil 11 is further strengthened, and the primary coil 11 can be prevented from falling off more reliably. In addition, the large three-dimensional portion hardly gets caught on the small three-dimensional portion already pushed out to form the frame, and good operability at the indwelling operation is obtained.

A quadrangle s1 seen from the common axis a1 of the virtual cylindrical body C1 of the middle solid 4A is a square, and a quadrangle s2 seen from the common axis a2 of the virtual cylindrical body C2 of the large solid 4B is also a square. The four planes F1 to F4 of the virtual cylindrical body C1 of the middle solid 4A are squares having the same size and shape as those of the quadrangle s1, and the curved parts 51a to 51e of the primary coil 11 are formed so as to substantially follow circular shapes inscribed in the squares of the planes F1 to F4. The four planes F5 to F8 of the virtual cylindrical body C2 of the large solid 4B are squares having the same size and shape as those of the quadrangle s2, and the curved parts 52a to 52f of the primary coil 11 are formed so as to substantially follow circular shapes inscribed in the squares of the planes F5 to F8. The squares mentioned herein refer to quadrangles, each of which has the same length of four sides and has an angle formed by adjacent sides of 90 degrees according to a general definition. However, in terms of the nature of the in vivo indwelling member formed of the spirally wound primary coil, the shape of the square does not necessarily have to conform to the definition of the square, and includes quadrangular shapes in which lengths and angles of sides are different from one another or the respective sides do not intersect one another.

As described above, the three-dimensional portions of the curved parts which substantially follow the circular shapes inscribed in the respective planes of the virtual cylindrical bodies C1/C2, each of which is surrounded by the squares of the same size. In this way, the three-dimensional portions spread so as to expand outward more uniformly according to the shape of the inner wall surface of the aneurysm or the like, a stable frame with high adhesion can be formed along the inner wall, and the indwelling density can also be further increased. Such a form is obtained by forming the four winding portions, which constitute each of the aggregates 7A/7B of the above-described mandrel 6, by the winding portions with the same circumferential length as described above.

The length of the primary coil that constitutes the three-dimensional portion excluding the largest three-dimensional portion, i.e., the middle solid 4A in this example, is preferably set to a length of 25% or more and 50% or less of the overall length of the primary coil. In this way, there is maintained a sufficient volume of the primary coil to enable the following actions to function, the actions are: to form a sufficient amount of the frame by the three-dimensional portion (middle solid 4A) pushed out previously; and in addition, to make it possible to form a frame excellent in adhesion by further spreading the frame to the inner wall side also with regard to the largest three-dimensional portion (large solid 4B) pushed out last. For the same reason, the length of the primary coil that constitutes the largest three-dimensional portion, that is, the large solid 4B in this example, is preferably set to 50% or more and 75% or less of the overall length of the primary coil.

With regard to a ratio of the areas of the quadrangles of the three-dimensional portions as seen from the common axes of the virtual cylindrical bodies, in which the three-dimensional portions are those having a relatively small area of the quadrangle and having a next large area thereof, that is, in this example, a ratio of the area of the quadrangle s1 of the virtual cylindrical body C1 of the middle solid 4A and the area of the quadrangle s2 of the virtual cylindrical body C2 of the large solid 4B, the ratio concerned is preferably set so that the area of the large solid 4B becomes 1.1 times or more and 2.3 times or less the area of the solid (middle solid 4A) having such a smaller area. In this way, the frame previously formed by the relatively small three-dimensional portion (middle solid 4A) is pushed and spread toward the inner wall side by the next large three-dimensional portion (large solid 4B), and such a firm frame along the inner wall of the aneurysm or the like is reliably formed. Moreover, there is considered a ratio of the lengths of the sides which constitute the quadrangles of the three-dimensional portions as seen from the common axes of the virtual cylindrical bodies, in which the three-dimensional portions are those having a relatively small area of the quadrangle and having a next large area thereof. When each of the quadrangles is a square as in this example, the above-described length is a length of a side thereof, and when the quadrangle is other than a square, the length is a length of a shortest side among four sides thereof. In this example, the above-described ratio is a ratio of the length of the quadrangle s1 of the virtual cylindrical body C1 of the middle solid 4A and the length of the quadrangle s2 of the virtual cylindrical body C2 of the large solid 4B. Here, the ratio of the length of the large three-dimensional portion (large solid 4B) to the length of the three-dimensional portion (middle solid 4A) having the smaller length is preferably set to 1.05 times or more and 1.5 times or less, more preferably, 1.1 times or more to 1.2 times or less. In this way, likewise, the frame previously formed by the relatively small three-dimensional portion (middle solid 4A) is pushed and spread toward the inner wall side by the next large three-dimensional portion (large solid 4B), and such a firm frame along the inner wall of the aneurysm or the like is reliably formed.

The anchor portion 40 formed of at least one loop-shaped curved part 50 may be formed in a region of the primary coil, the region leading to the tip of the primary coil more on the tip end side than the smallest three-dimensional portion (middle solid 4A). In this example, only one loop-shaped curved part 50 is formed, and the spiral part 53 leading to the middle solid 4A is formed continuously therewith.

The spiral part 53 is formed by winding the primary coil around the sloped notch groove 61a of the mandrel 6. A length of the primary coil that constitutes the anchor portion 40 is set to a length less than 15% of the overall length of the primary coil. When the anchor portion 40 is longer than 15%, retention stability with respect to the inner wall is reduced, and a function thereof as an anchor decreases. Particularly, the length of the anchor portion is preferably 5% or more and 10% or less with respect to the overall length of the primary coil. Note that, the length of the primary coil that constitutes the anchor portion is preferably shorter than the length of the primary coil that constitutes the middle solid.

Hereinafter, with reference to FIGS. 5 to 9, a description will be made based on a specific procedure until the secondary shape is formed by winding the primary coil around the mandrel 6 according to this embodiment.

In this example, the primary coil is wound and formed in order from the anchor portion that serves as the tip end side. However, as mentioned above, the primary coil can be wound and formed in order from the large solid side on the base end side. First, a core wire 12 longer than the overall length of the primary coil is preferably inserted into the lumen of the primary coil 11. A material of the core wire is not particularly limited, and for example, stainless steel can be used. A diameter of the core wire is appropriately selectable depending on the purpose of use, and is not particularly limited.

Then, a protruding end portion on a front end side of the core wire 12 is fixed at a desired position of the winding portion 70 which is a start of winding on one end side of the mandrel 6. In this example, an attachment screw 79 for fixing is provided at an end portion of the winding portion 70. The core wire 12 is sandwiched between a head portion of the screw 79 and an outer surface of the winding portion 70, is tightened by the screw 79, and is thereby fixed. Other fixing means such as a tape and a clip which are resistant to high temperatures may be used. Moreover, the primary coil may be fixed outside the mandrel 6.

Next, the primary coil 11 is wound around the winding portion 70 of the mandrel 6 while applying tension thereto as necessary, the primary coil 11 is wound around about one turn (360 degrees), and the primary coil 11 is wound a half turn in a spiral shape toward the winding portion 71 while being engaged in the sloped notch groove 61a formed in the stepped portion 60a between the winding portion 70 and the winding portion 71. In this way, the primary coil 11 reaches a continuous portion of the winding portion 71 and the winding portion 72 of the aggregate 7A on the mandrel 6.

In the process so far, the anchor portion 40 including the loop-shaped curved part 50 (loop-shaped part R01) and spiral part 53 of the primary coil is formed. Only one loop-shaped part (R01) is formed in the anchor portion 40. The loop-shaped part R01 formed by being wound around the winding portion 70 having the shortest circumferential length is a loop-shaped part having the shortest loop length. The loop-shaped part R01 has highest flexural rigidity among the loops formed by the primary coil, and is optimal as an anchor to be quickly and stably held on the inner wall of an aneurysm or the like. Here, the flexural rigidity indicates easiness of bending deformation, and the bending deformation is less likely to occur as the flexural rigidity is higher. Since the loop-shaped part R01 is formed by the winding portion with the smallest diameter in this example, the flexural rigidity thereof becomes higher than those in other three-dimensional portions.

Next, as shown in FIG. 7, when the primary coil 11 is wound about a half turn (180 degrees) along the winding portion 72, the primary coil 11 reaches a continuous portion of the winding portion 72 and the winding portion 74 on the mandrel 6. Moreover, the primary coil 11 is wound about one turn around the winding portion 74. Moreover, when the primary coil 11 is wound about a half turn around the winding portion 72, the primary coil 11 returns to the continuous portion of the winding portion 72 and the winding portion 71. Then, the primary coil 11 is wound about a half turn around the winding portion 71.

At this time, intersecting the curved part 51a of the primary coil previously wound spirally along the sloped notch groove 61a from the winding portion 70 and wound around the winding portion 72, the primary coil 11 to be wound around the winding portion 71 further passes on the curved part 51a. In this way, looseness of the spiral part 53 wound along the notch groove 61a is prevented. Moreover, when the primary coil 11 is wound about a half turn around the winding portion 73, the primary coil 11 reaches a vicinity of the continuous portion of the winding portion 73 and the winding portion 74.

The shape of the middle solid 4A is formed by the process so far. In the middle solid 4A, the curved part 51d that makes about a half turn is formed on the winding portion 71. In addition, the curved part 51a that makes about a half turn and the curved part 51c that makes about a half turn are located on the winding portion 72, and an annular ring that makes about one turn is formed by combining these parts with each other. In addition, the curved part 51e that makes about a half turn is formed on the winding portion 73, and the loop-shaped curved part 51b (loop-shaped part R11) which makes about one turn is formed on the winding portion 74. In this manner, only one loop-shaped part (R11) is formed in the middle solid 4A.

Next, from the winding portion 74 toward the winding portion 75, a connecting part 54 of the primary coil 11 is disposed while being passed through the notch groove 61b provided in the stepped portion 60b between the winding portion 74 and the winding portion 75, and the primary coil 11 is wound as it is about one turn around the winding portion 77 of the aggregate 7B. In this way, the primary coil returns to a continuous portion of the winding portion 77 and the winding portion 75, and then, is wound about a half turn around the winding portion 75. At this time, as also shown in FIGS. 6(a) and 6(b), the primary coil passes on the connecting part 54 passing through the inside of the notch groove 61b, and the curved part 52b is formed on the winding portion 75. The curved part 52b can pass over the connecting part 54 without interfering therewith, and a bent portion is prevented from being formed, and looseness of the connecting part 54 is prevented by pressing the connecting part 54 by the curved part 52b.

When the primary coil 11 reaches a continuous portion of the winding portion 75 and the winding portion 76, then the primary coil 11 is wound about a half turn around the winding portion 76, is thereafter wound about one turn around the winding portion 78, is further wound about a half turn around the winding portion 76, and is finally wound about one turn around the winding portion 75. The length of the primary coil 11 is set in advance so that the rear end thereof comes at this last winding around the winding portion 75. When winding the primary coil 11 around the winding portion 75, the primary coil 11 further passes on the connecting part 54 in the notch groove 61b as shown in FIGS. 6(a) and 6(b). In the same way as described above, a bent portion is prevented from being formed in the loop-shaped part 52f formed in the above manner, and in addition, the connecting part 54 is pressed, and is more reliably prevented from being loosened.

Then, the core wire 12 extending from the base end of the primary coil is appropriately wound around the winding portion 75 and the winding portions 77 and 78 so that the primary coil 11 is not loosened, and finally, is fixed to an attachment screw 80 for fixing, which is provided at an end portion of the winding portion 78 on the other end side of the mandrel 6. The shape of the large solid 4B is formed by the process so far, and the intermediate shape is obtained.

In the large solid 4B, the curved part 52b of about a half turn and the loop-shaped curved part 52f (loop-shaped part R23) of about one turn are formed side by side on the winding portion 75. Further, the curved part 52c of about a half turn and the curved part 52e of about a half turn are located on the winding portion 76, and an annular ring of about one turn is formed by combining both of the parts with each other. In addition, the loop-shaped curved part 52a (loop-shaped part R21) of about one turn is formed on the winding portion 77, and the loop-shaped curved part 52d (loop-shaped part R22) of about one turn is formed on the winding portion 78. As described above, three loop-shaped parts (R21, R22, R23) are formed in the large solid 4B.

The number of times the primary coil is wound around the winding portion of the anchor portion 40, the middle solid 4A, the large solid 4B, or the like, that is, the number of loops formed in the winding portion may be plural, instead of one loop. In addition to the loop that extends one or more turns to form a loop, there may be provided such a curved part that does not form a loop that extends less than one turn, which has an arc shape that extends less than one turn and does not form a loop. In addition, there may be provided an annular ring constituent portion that is a constituent portion formed by combining a plurality of the curved parts as described above. Pluralities of the curved parts and the annular ring constituent portions may be included in one winding portion.

Then, the primary coil 11 wound around the mandrel 6 is heated together with the mandrel 6 with the core wire 12 internally mounted, and is given the intermediate shape including the anchor portion 40, the middle solid 4A, and the large solid 4B, which are formed by winding the primary coil 11 around the mandrel 6 (heat treatment (firing)). Heating conditions can be determined as appropriate depending on the material of the primary coil 11. For example, a heating temperature is preferably 400° C. or more, and a heating time is preferably 15 minutes or more. The heating temperature preferably is 750° C. or lower. When the heating temperature is higher than 750° C., a Pt coil tends to become brittle and easily broken. Although there is no upper limit of the heating time, the heating time is preferably 3 hours or shorter for the productivity of manufacturing. Thereafter, when the primary coil 11, in which the core wire 12 is still internally mounted, is removed from the mandrel 6, the intermediate-shape coil 2 having the intermediate shape shown in FIG. 8 is obtained. In a different aspect of the present invention, this intermediate shape can be defined as a final secondary shape of the in vivo indwelling member.

The procedure of winding the primary coil around the mandrel 6, which is described above, is merely an example, and other winding procedures are of course possible. Further, although the number of turns in the mode of winding the primary coil around one rod-shaped portion by one winding is set to about a half turn and about one turn, the number of turns is not limited to this, and may be less than a half turn, a ¾ turn, or two turns or more.

Next, as shown in FIGS. 9(*a*) and 9(*b*), a part of the primary coil located between the middle and large solids of the coil in the intermediate shape, which is removed from the mandrel, is bent. In this way, there is created the secondary coil having the secondary shape in which the middle solid 4A and the anchor portion 40 are disposed inside the large solid 4B of the intermediate-shape coil 2. It should be noted that the core wire 12 is inserted in the lumen of the intermediate-shape coil and the secondary coil shown in the drawings. Specifically, the middle solid 4A and the large solid 4B are disposed so that the axis a1 of the middle solid 4A and the axis a2 of the large solid 4B substantially coincide with each other, and the planes of the virtual cylindrical bodies C1 and C2 are rotated relative to each other by a predetermined angle, by 45 degrees in this example, so as not to be parallel to each other. This is the final secondary shape. In the present invention, the intermediate-shape coil can be deformed, heated, and given the shape. In giving the shape to the intermediate-shape coil, another three-dimensional portion can be disposed inside one three-dimensional portion of the intermediate-shape coil. In order to dispose the other three-dimensional portion inside one three-dimensional portion, the primary coil, which is located between the respective solids and forms a loop and the part between the loops, is bent, whereby another three-dimensional portion can be disposed inside one three-dimensional portion. In particular, preferably, such disposition is made so that the common axis of the one three-dimensional portion in which the other three-dimensional portion is disposed therein and the common axis of the other three-dimensional portion are parallel to each other. By making the disposition as described above, the adhesion of the coil to the inner wall of an aneurysm or the like can be enhanced. Note that the disposition in which the common axes of the three-dimensional bodies are parallel to each other includes a disposition in which the common axes of the three-dimensional bodies are coaxial with each other. In this example, the middle solid and the anchor portion are disposed inside the large solid in a state of being rotated by 45 degrees. However, the large solid can be disposed inside the middle body, and such a rotational angle can be appropriately selected, for example, can be set to 90 degrees. The intermediate-shape coil in a state of being detached from the mandrel with the core wire 12 left inserted into the lumen also has flexibility, and can be bent at an arbitrary position. At this time, structures and functions of the anchor portion 40, the middle solid 4A, and the large solid 4B formed in the intermediate-shape coil 2 are not substantially changed or damaged, and only mutual disposition thereof is changed in shape.

By further heating (heat treatment (firing)) the intermediate-shape coil in this state, the secondary shape is given thereto. Heating conditions can be determined as appropriate depending on the material of the primary coil 11. For example, a heating temperature is preferably 400° C. or more, but it is preferable to set the heating temperature to a temperature higher than the heating temperature at the time of providing the intermediate shape. The heating temperature is preferably 750° C. or lower. When the heating temperature is higher than 750° C., a Pt coil tends to be brittle and easily broken. Although there is no upper limit of the heating time, the heating time is preferably 3 hours or shorter for the productivity of manufacturing. A heating time is preferably 15 minutes or more. In this heat treatment, for example, a mold having a lumen corresponding to the secondary shape, in this example, a lumen in the shape of a regular cube, or the like can be used. It is preferable that heating temperature of the mold is higher than temperature of the mandrel (as explained above). The difference in heating temperature between the mandrel and the mold is preferably 50 to 300° C., more preferably 70 to 200° C. The heating temperature of the mold is preferably higher than that of the mandrel by 50 to 300° C., thereby applying the residual stress to the shape of the secondary coil in the state of being inserted in the lumen of the mold (even after cooled down). It is preferable that the heating temperature of a mold, into which the secondary coil is inserted, is higher than the heating temperature to effectively provide the primary coil with a secondary coil shape. After performing the heat treatment, the shaping mold is cooled. A cooling method is not particularly limited. It is preferred to perform the cooling by a general method, for example, by leaving the shaping mold to stand at room temperature. After the shaping mold is cooled, an in-vivo indwelling member having a three-dimensional structure that corresponds to the structure of the inner hollow section can be obtained from the inside of the shaping mold. One of two or more three-dimensional portions may be first placed in the mold, and then another one of the three-dimensional portions may be placed in the one that has been already placed in the mold.

After the heat treatment, the secondary coil 3 is obtained by removing the core wire 12. The secondary coil from which the core wire 12 is removed may be in a state in which the given shape is maintained or in a state in which the given shape is not maintained. When pushed out into the aneurysm or the like, such a secondary-shape coil thus disposed can further press and expand the frame, which is formed by the already developed small three-dimensional portion, toward the inner wall side more reliably by the largest three-dimensional portion, and can further enhance the adhesion and the indwelling density. Into the secondary coil from which the core wire is removed, an internal wire is inserted instead of core wire. A tip end portion is formed by forming a tip end chip or the like on one end of the secondary coil. A disposing wire or the like is coupled to the other end of the secondary coil via a coupling member or the like. In this way, an in vivo indwelling member placement device can be manufactured.

In this embodiment, one loop-shaped part R01 of the anchor portion 40, one loop-shaped part R11 of the middle solid 4A, and three loop-shaped parts R21 to R23 of the large solid 4B are formed from the tip end side of the secondary-shape coil. The circumferential lengths of the winding portions are gradually set longer in order of the anchor portion 40, the middle solid 4A, and the large solid 4B. Accordingly, the loop lengths of the loop-shaped parts also become longer correspondingly. Only one loop-shaped part R01 of the anchor portion 40 having the shortest loop length is provided, whereby the anchor effect can be ensured. Moreover, two or more loop-shaped parts (R21 to R23) of the large solid 4B having the longest loop length are provided, whereby the effect of enhancing the adhesion by pressing and expanding the part of the coil, which is pushed out previously, is sufficiently obtained.

Such a secondary coil 3 becomes the in vivo indwelling member 1. For example, in the in vivo indwelling member 1, an in vivo indwelling member placement wire (92) is connected via the coupling member (91) on the base end side thereof, whereby the in vivo indwelling member placement device (90) is formed. As the coupling member, a known one configured so that the in vivo indwelling member 1 can be separated and indwelled inside the aneurysm or the like can be widely adopted. For example, the coupling member is made of a thermally soluble material which is heated, melted, and cut by high frequency power applied through such an in vivo indwelling wire. An internal wire (not shown) for preventing extension of the secondary coil can be provided inside the in vivo indwelling member. A material of the internal wire is not particularly limited, and examples thereof include a simple substance such as platinum, tungsten, iridium, tantalum, gold, and stainless steel, or an alloy formed by combining at least two of these, which are materials similar to those of the wire that forms the primary coil. The internal wire and the wire may be made of the same material or different materials. As the material of the internal wire, in addition to the above-described metals, resin and other materials can be used. Examples of the material include a simple substance such as polypropylene, polyethylene terephthalate, nylon, polyethylene, polylactic acid, polytetrafluoroethylene, and silk, and a material formed by combining at least these. The metal material and the resin material can be used in combination. A diameter of the internal wire is appropriately selectable depending on the purpose of use or the like, and is not particularly limited. For the internal wire, a single wire may be used as it is, or a stranded wire may be used. Moreover, the internal wire may be in the form of a straight line, or may be a wavy line, a spiral line, or a curve, which has a wavelength or amplitude, each corresponding to the purpose of use.

The in vivo indwelling member placement device is inserted into the lumen of the delivery catheter (not shown). By operating the base end side of the in vivo placement wire, the in vivo indwelling member 1 on the tip side is pushed out from the tip end opening of the delivery catheter into the aneurysm or the like. Then, the in vivo indwelling member 1 is sequentially loaded into the above-mentioned secondary shape, and can be indwelled by cutting the coupling member. The in vivo indwelling member can flexibly change the shape thereof along the shape of the aneurysm or the blood vessel, which are to be filled therewith. The in vivo indwelling member 1 pushed out into the inside of the aneurysm or the like, which occurs in the parent blood vessel in the living body, embolizes the aneurysm concerned, so that the in vivo indwelling member 1 is also called a vascular embolization coil.

Figure 12:
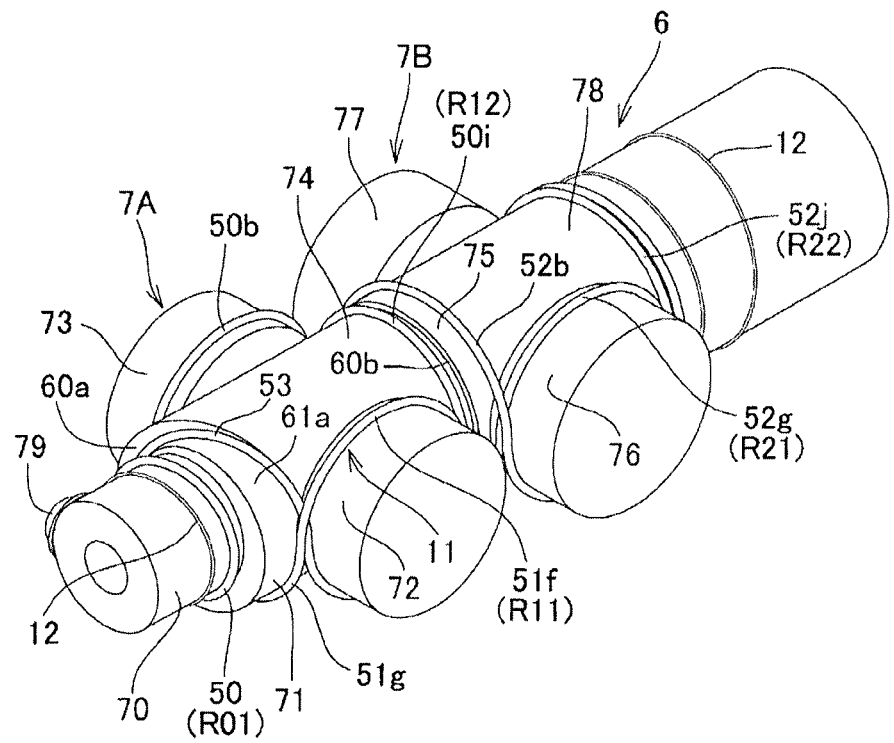
FIG. 12 is a perspective view showing a modified example of a state in which the primary coil is wound around the mandrel as seen from a lower surface side thereof.
Figure 13:
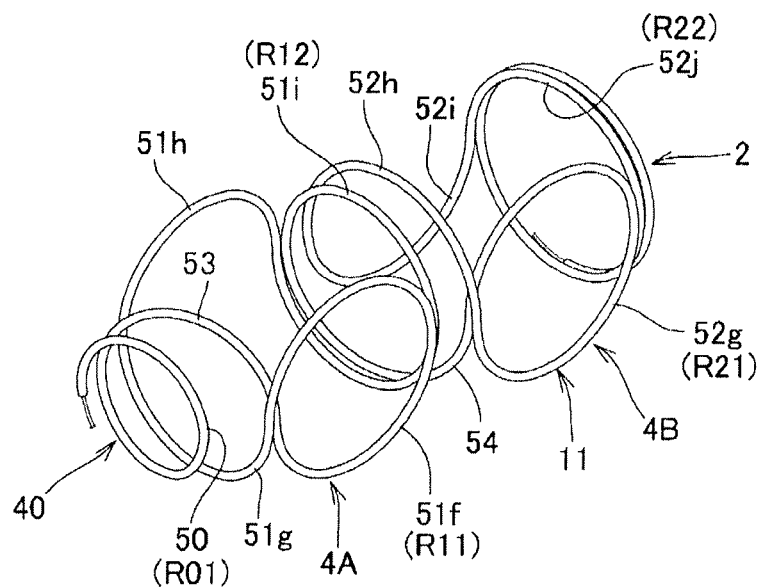
FIG. 13 is a perspective view showing a modified example of the shape of the intermediate-shape coil formed by the mandrel.

FIGS. 12 and 13 show a modified example in which the winding form of the primary coil 11, that is, the intermediate shape is changed while using the mandrel 6 having the same structure as described in the representative embodiment.

As shown in FIG. 13, in the intermediate shape of this modified example, curved parts 50, 51f to 51i and 52g to 52j in the primary coil 11, which are curved and extend continuously on substantially the same plane, are formed to have a three-dimensional shape. In this example, two three-dimensional portions, i.e., the three-dimensional portion (middle solid 4A) formed by continuously providing at least four curved parts 51f to 51i over four planes; and the three-dimensional portion (large solid 4B) formed by continuously providing at least four curved parts 52g to 52j over four planes, are formed by the aggregates 7A and 7B of the mandrel 6, respectively.

Similar to the example of the above-mentioned representative embodiment, with regard to the four planes of each of the three-dimensional portions, all of the normal directions thereof are perpendicular to a predetermined common axis direction. Each of the curved parts (51f to 51i, 52g to 52j) which constitute the respective three-dimensional portions (middle solid 4A, large solid 4B) is formed in any of the respective planes of the quadrangular virtual cylindrical bodies as seen from the common axes surrounded by the four planes. In addition, the intermediate-shape coil of this example is processed into such a secondary shape in which the anchor portion 40 and the middle solid 4A are disposed inside the large solid 4B, and the middle solid 4A and the large solid 4B are sequentially developed inside the aneurysm or the like.

Specifically, similar to the example of the above-mentioned representative embodiment, the protruding end portion on the front end side of the core wire 12 of the primary coil 11 is fixed to the attachment screw 79 of the winding portion 70 of the mandrel 6. The primary coil 11 is wound around the winding portion 70. The primary coil 11 is wound around one turn (360 degrees). The primary coil 11 is wound about a half turn in a spiral shape toward the winding portion 71 while being engaged in the sloped notch groove 61a formed in the stepped portion between the winding portion 70 and the winding portion 71. In this way, the anchor portion 40 including the loop-shaped curved part 50 (loop-shaped part R01) and the spiral part 53 is formed.

Next, as shown in FIG. 12, the primary coil 11 is wound about one turn (360 degrees) along the winding portion 72, and then the primary coil 11 reaches a continuous portion of the winding portion 72 and the winding portion 71 on the mandrel 6. Moreover, the primary coil 11 is wound about a half turn around the winding portion 71. At this time, intersecting the curved part 51f of the primary coil previously wound spirally along the sloped notch groove 61a from the winding portion 70 and wound around the winding portion 72, the primary coil 11 to be wound around the winding portion 71 further passes on the curved part 51ƒ In this way, looseness of the spiral part 53 wound along the notch groove 61a is prevented.

Moreover, when the primary coil 11 is wound about a half turn around the winding portion 73, the primary coil 11 reaches a vicinity of the continuous portion of the winding portion 73 and the winding portion 74. Then the primary coil 11 is further wound about one and a half turns around the winding portion 74, whereby the shape of the middle solid 4A is formed. In the middle solid 4A, the loop-shaped curved part 51ƒ (loop-shaped part R11) which makes about one turn is formed on the winding portion 72, and the curved part 51g that makes about a half turn is formed on the winding portion 71. In addition, the curved part 51h that makes about a half turn is formed on the winding portion 73, and the loop-shaped curved part 51i (loop-shaped part R12) which makes about one and a half turns is formed on the winding portion 74. In this manner, two loop-shaped parts (R11, R12) are formed in the middle solid 4A.

Next, from the winding portion 74 toward the winding portion 76, a connecting part 54 of the primary coil 11 is disposed while being passed through the notch groove 61b provided in the stepped portion 60b therebetween, and the primary coil 11 is wound as it is about one turn around the winding portion 76 of the aggregate 7B. In this way, the primary coil returns to a continuous portion of the winding portion 76 and the winding portion 75, and then, is wound about a half turn around the winding portion 75. At this time, the primary coil passes on the connecting part 54 passing through the inside of the notch groove 61b, and the curved part 52h is formed on the winding portion 75. The curved part 52h can pass over the connecting part 54 without interfering therewith, and a bent portion is prevented from being formed, and looseness of the connecting part 54 is prevented by pressing the connecting part 54 by the curved part 52h.

When the primary coil 11 reaches the continuous portion of the winding portion 75 and the winding portion 77, then the primary coil 11 is wound about a half turn around the winding portion 77, and thereafter, is wound one turn or more around the winding portion 78. The length of the primary coil 11 is set in advance so that the rear end thereof comes at this last winding around the winding portion 78. Then, the core wire 12 extending from the base end of the primary coil is fixed to the attachment screw 80 while being wound around the winding portion 78. The shape of the large solid 4B is formed by the process so far, and the intermediate shape is obtained.

In the large solid 4B, the curved part 52g (loop-shaped part R21) which makes about one turn is formed on the winding portion 76, and the curved part 52h that makes about a half turn is formed on the winding portion 75. In addition, the curved part 52i that makes about a half turn is formed on the winding portion 77, and the loop-shaped curved part 52j (loop-shaped part R22) which makes about one turn is formed on the winding portion 78. In this manner, two loop-shaped parts (R21, R22) are formed in the large solid 4B.

Then, in a state of being wound around the mandrel 6, the primary coil 11 is heated to obtain the intermediate-shape coil 2 including the anchor portion 40, the middle solid 4A, and the large solid 4B as shown in FIG. 13. It should be noted that the core wire 12 is inserted in the lumen of the intermediate-shape coil and the secondary coil shown in the drawings. Thereafter, similar to the example of the above-mentioned representative embodiment, the middle solid 4A and the large solid 4B are disposed and heated so that the axis of the middle solid 4A and the axis of the large solid 4B substantially coincide with each other, and that the planes of the virtual cylindrical bodies thereof are rotated by 45 degrees around an axial center so as not to be parallel to each other. In this way, a secondary shape (not shown) is obtained, and the core wire 12 is removed to form the secondary coil, that is, the in vivo indwelling member. Also with regard to this in vivo indwelling member, although not shown, the in vivo indwelling member placement device is formed in which the in vivo indwelling member placement wire is connected to the base end side via the coupling member.

FIGS. 14 to 17 show another modified example in which the winding form of the primary coil 11, that is, the intermediate shape is changed while using the mandrel 6 having the same structure as described in the representative embodiment. In these figures as well, the shape of the secondary coil and the intermediate shape, which are not accompanied by the mandrel, illustrate such a state in which the reinforcement core material (core wire) is inserted into the lumen of the primary coil.

Figure 15:
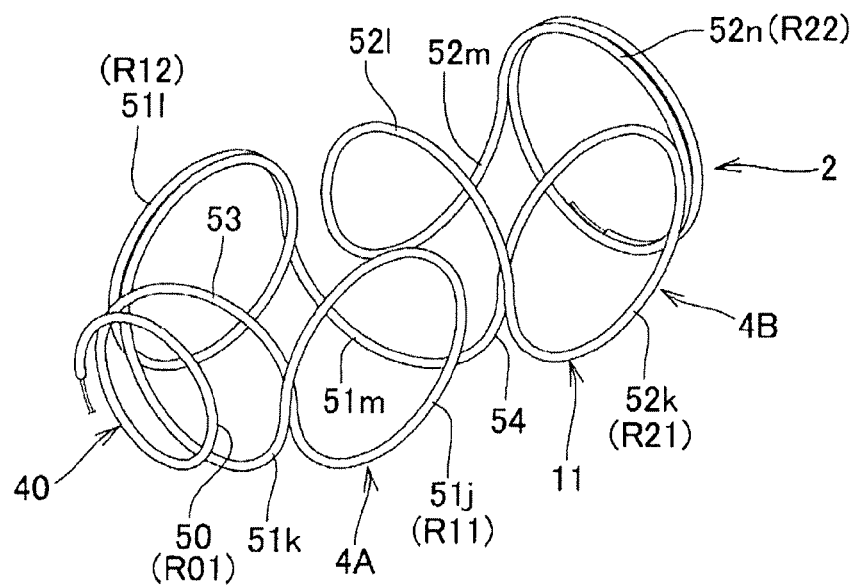
FIG. 15 is a perspective view showing the other modified example of the shape of the intermediate-shape coil formed by the mandrel.

As shown in FIG. 15, in the intermediate shape of this modified example, curved parts 50, 51j to 51m and 52k to 52n in the primary coil 11, which are curved and extend continuously on substantially the same plane, are formed to have a three-dimensional shape. In this example, two three-dimensional portions, i.e., the three-dimensional portion (middle solid 4A) formed by continuously providing at least four curved parts 51j to 51m over four planes; and the three-dimensional portion (large solid 4B) formed by continuously providing at least four curved parts 52k to 52n over four planes, are formed by the aggregates 7A and 7B of the mandrel 6, respectively.

Figure 16A:
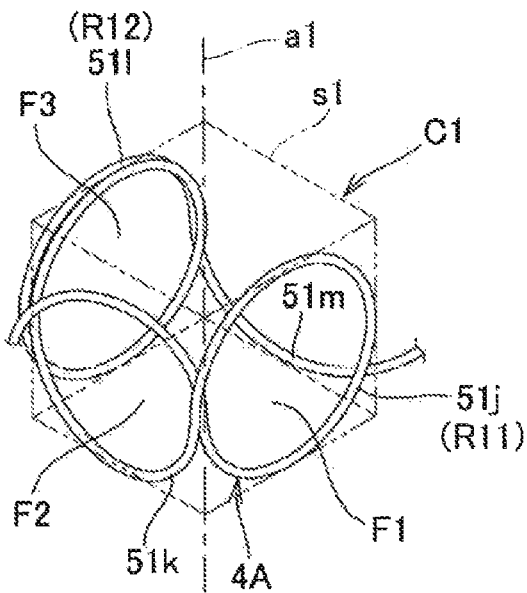
FIGS. 16(a) and 16(b) are explanatory diagrams for explaining configurations of middle and large solids in the intermediate-shape coil and the secondary coil according to the other modified example by using a virtual cylindrical body.
Figure 16B:
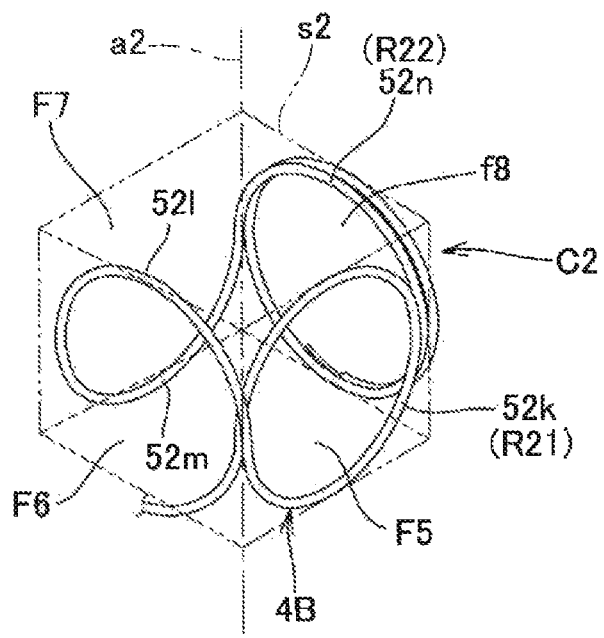

As shown in FIG. 16, similar to the example of the above-mentioned representative embodiment, with regard to the four planes of each of the three-dimensional portions, all of the normal directions thereof are perpendicular to a predetermined common axis a1/a2 direction. Each of the curved parts (51j to 51m, 52k to 52n) which constitute the respective three-dimensional portions (middle solid 4A, large solid 4B) is formed in any of the respective planes of the quadrangular virtual cylindrical bodies C1/C2 as seen from the common axes surrounded by the four planes. In addition, the intermediate-shape coil of this example is processed into such a secondary shape in which the anchor portion 40 and the middle solid 4A are disposed inside the large solid 4B, and the middle solid 4A and the large solid 4B are sequentially developed inside the aneurysm or the like.

Figure 14:
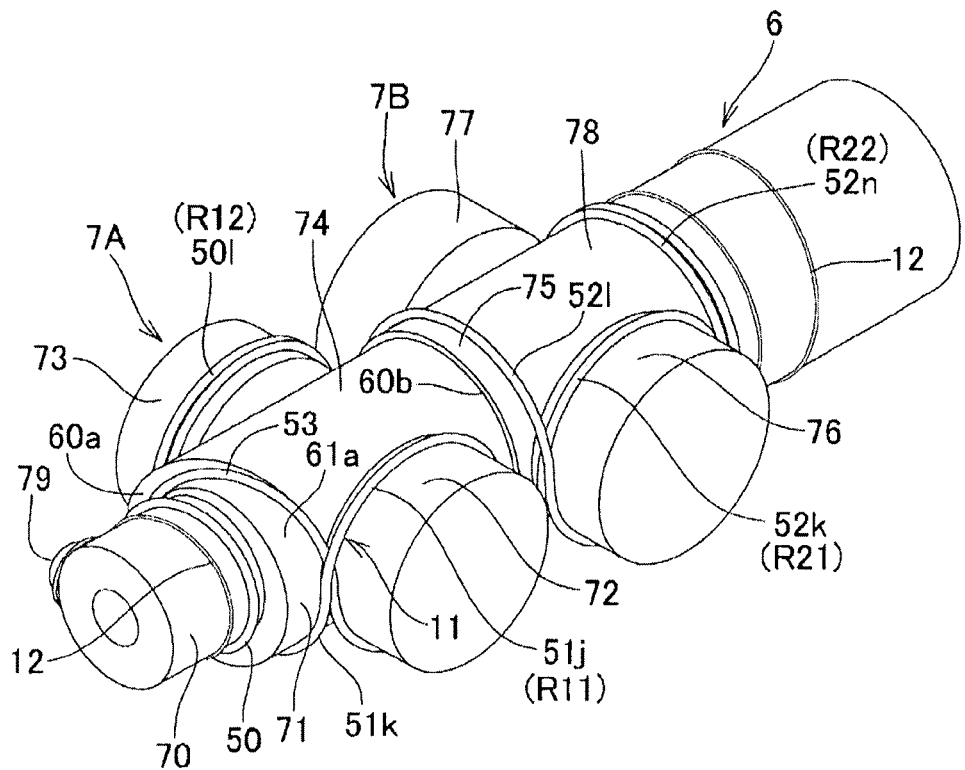
FIG. 14 is a perspective view showing another modified example of the state in which the primary coil is wound around the mandrel as seen from a lower surface side thereof.

Specifically, as shown in FIG. 14, similar to the example of the above-mentioned representative embodiment, first, the protruding end portion on the front end side of the core wire 12 of the primary coil 11 is fixed to the attachment screw 79 of the winding portion 70 of the mandrel 6. The primary coil 11 is wound around the winding portion 70. The primary coil 11 is wound around one turn (360 degrees). The primary coil 11 is wound about a half turn in a spiral shape toward the winding portion 71 while being engaged in the sloped notch groove 61a formed in the stepped portion between the winding portion 70 and the winding portion 71. In this way, the anchor portion 40 including the loop-shaped curved part 50 (loop-shaped part R01) and the spiral part 53 is formed.

Next, the primary coil 11 is wound about one turn (360 degrees) along the winding portion 72, and then the primary coil 11 reaches a continuous portion of the winding portion 72 and the winding portion 71 on the mandrel 6. Moreover, the primary coil 11 is wound about a half turn around the winding portion 71. At this time, intersecting the curved part 51*j* of the primary coil which is previously wound spirally along the sloped notch groove 61*a* from the winding portion 70 and wound around the winding portion 72, the primary coil 11 to be wound around the winding portion 71 further passes on the curved part 51*j*. In this way, looseness of the spiral part 53 wound along the notch groove 61*a* is prevented.

Moreover, the primary coil 11 is wound abut one and a half turns around the winding portion 73, and is further wound about a half turn around the winding portion 74, whereby the shape of the middle solid 4A is formed. In the middle solid 4A, the loop-shaped curved part 51*j* (loop-shaped part R11) which makes about one turn is formed on the winding portion 72, and the curved part 51*k* that makes about a half turn is formed on the winding portion 71. Furthermore, the curved part 51*l* (loop-shaped part R12) which makes about one and a half turns is formed on the winding portion 73, and the curved part 51*m* that makes about a half turn is formed on the winding portion 74. In this manner, two loop-shaped parts (R11, R12) are formed in the middle solid 4A.

Next, from the winding portion 74 toward the winding portion 76 of the aggregate 7B, a connecting part 54 of the primary coil 11 is disposed while being passed through the notch groove 61*b* provided in the stepped portion 60*b* between the winding portion 74 and the winding portion 76, and the primary coil 11 is wound as it is about one turn around the winding portion 76. Next, the primary coil 11 is wound about a half turn around the winding portion 75, and at this time, the primary coil passes on the connecting part 54 passing through the inside of the notch groove 61*b*, and the curved part 52*l* is formed on the winding portion 75. The curved part 52*l* can pass over the connecting part 54 without interfering therewith, and a bent portion is prevented from being formed, and looseness of the connecting part 54 is prevented by pressing the connecting part 54 by the curved part 52*l*.

When the primary coil 11 reaches the continuous portion of the winding portion 75 and the winding portion 77, then the primary coil 11 is wound about a half turn around the winding portion 77, and thereafter, is wound one turn or more around the winding portion 78. The length of the primary coil 11 is set in advance so that the rear end thereof comes at this last winding around the winding portion 78. Then, the core wire 12 extending from the base end of the primary coil is fixed to the attachment screw 80 while being wound around the winding portion 78. The shape of the large solid 4B is formed by the process so far, and the intermediate shape is obtained.

In the large solid 4B, the curved part 52*k* (loop-shaped part R21) which makes about one turn is formed on the winding portion 76, and the curved part 52*l* that makes about a half turn is formed on the winding portion 75. In addition, the curved part 52*m* that makes about a half turn is formed on the winding portion 77, and the loop-shaped curved part 52*n* (loop-shaped part R22) which makes about one and a half turns is formed on the winding portion 78. In this manner, two loop-shaped parts (R21, R22) are formed in the large solid 4B.

Figure 17A:
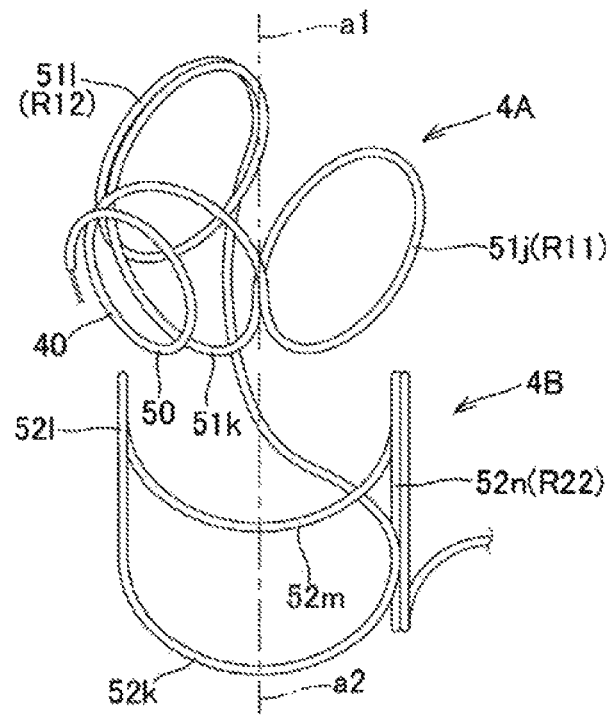
FIG. 17(a) is an explanatory diagram showing a state in which a middle solid and an anchor portion of the intermediate-shape coil according to the other modified example are disposed inside a large solid.
Figure 17B:
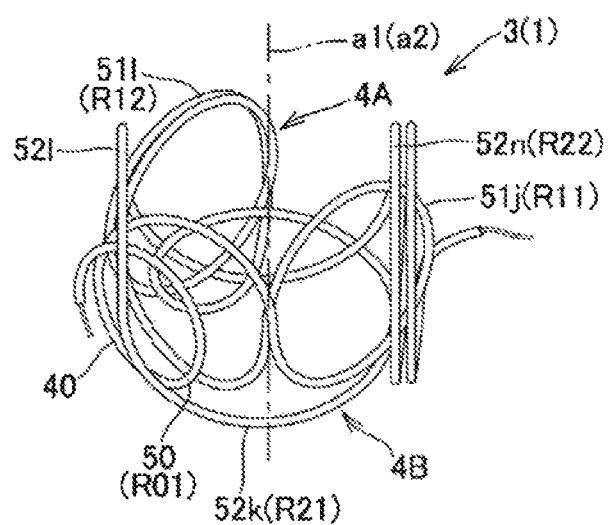
FIG. 17(b) is a perspective view showing a shape of a secondary coil (in vivo indwelling member) having the above disposition.

Then, in a state of being wound around the mandrel 6, the primary coil 11 is heated to obtain the intermediate-shape coil 2 including the anchor portion 40, the middle solid 4A, and the large solid 4B as shown in FIG. 15. Thereafter, similar to the example of the above-mentioned representative embodiment, as shown in FIG. 17(*a*), the middle solid 4A and the large solid 4B are disposed and heated so that the axis of the middle solid 4A and the axis of the large solid 4B substantially coincide with each other, and that the planes of the virtual cylindrical bodies thereof are rotated by 45 degrees around an axial center so as not to be parallel to each other. In this way, a secondary shape as shown in FIG. 17(*b*) is obtained, and the core wire 12 is removed to form the secondary coil, that is, the in vivo indwelling member. Also with regard to this in vivo indwelling member, although not shown, the in vivo indwelling member placement device is formed in which the in vivo indwelling member placement wire is connected to the base end side via the coupling member.

Figure 18A:
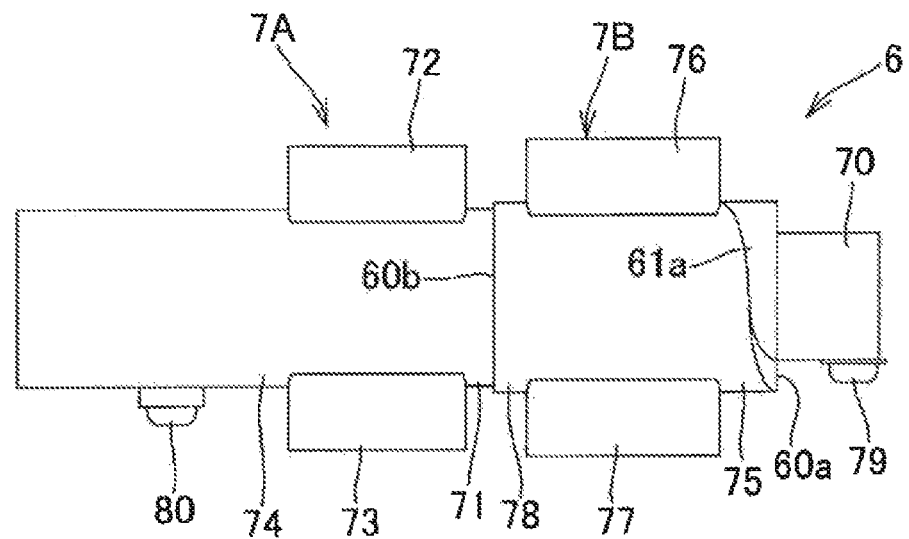
FIG. 18(a) is a front view showing a modified example of the mandrel as seen from above.
Figure 18B:
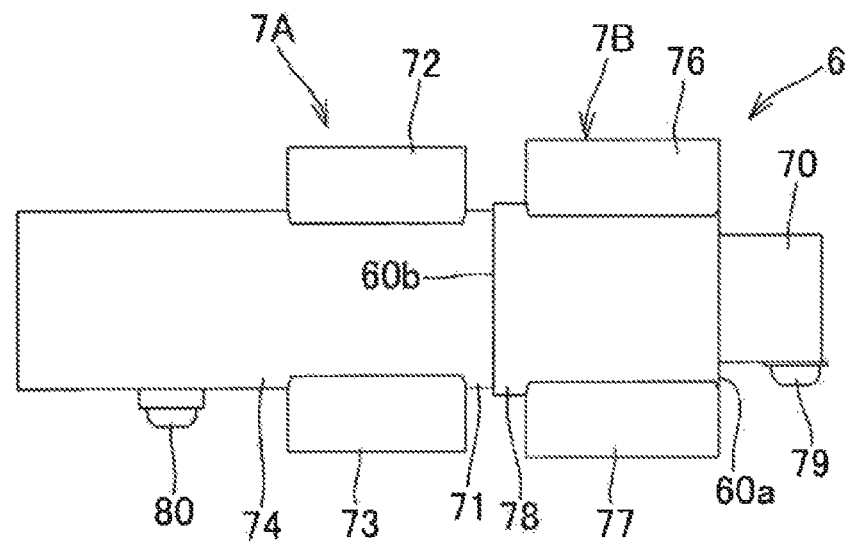
FIG. 18(b) is a front view showing still another modified example of the mandrel as seen from above.
Figure 19:
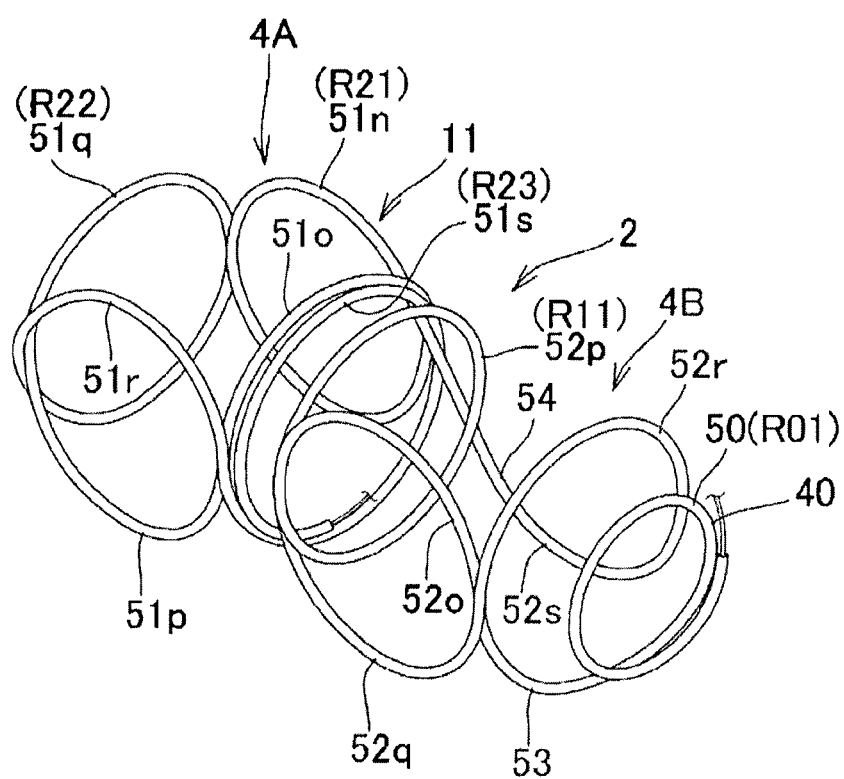
FIG. 19 is a perspective view showing a shape of an intermediate-shape coil formed by the mandrel according to the modified example.

FIGS. 18 to 20 show a mandrel different in structure from the mandrel 6 described in the representative embodiment, specifically, a mandrel including, in order from one end side thereof, the winding portion 70 for forming an anchor portion, the aggregate 7B for forming the large solid 4B, and the aggregate 7A for forming the middle solid 4A. Moreover, FIGS. 18 to 20 show a modified example in which the intermediate-shape coil 2 and the secondary coil 3 are formed by using the mandrel. In these figures as well, the shape of the secondary coil and the intermediate shape, which are not accompanied by the mandrel, illustrate such a state in which the reinforcement core material (core wire) is inserted into the lumen of the primary coil.

In the mandrel of this example, as shown in FIG. 18(*a*), stepped portions 60*a* and 60*b* are provided at predetermined positions through which the primary coil 11 passes by winding, and the stepped portion 60*a* is provided with a sloped notch groove 61*a* for receiving the primary coil 11. However, as shown in FIG. 18(*b*), the notch groove 61*a* may be omitted.

The mandrel 6 includes two aggregates, which are the aggregate 7A including the winding portions 71 to 74 in which circumferential lengths of outer circumferential surfaces are substantially the same, and the aggregate 7B including the winding portions 75 to 78 in which circumferential lengths of outer circumferential surfaces are substantially the same. The configurations and modified examples of the respective aggregates 7A and 7B are the same as those of the mandrel 6 of the above-mentioned representative embodiment. In this example, the aggregate 7A in which the circumferential length s of the respective winding portions are relatively short and the aggregate 7B in which the circumferential lengths of the respective winding portions are relatively long are reversed in order. The circumferential length of the respective winding portions 75 to 78 of the aggregate 7B is preferably set to 1.05 times or more to 1.5 times or less the circumferential length of the respective winding portions 71 to 74 of the aggregate 7A, more preferably, 1.1 times or more to 1.2 times or less the circumferential length.

Moreover, in addition to the aggregates 7A and 7B, more aggregates may be continuously provided to the mandrel of this example. In this case, in a part of the aggregates of the plurality of aggregates, circumferential lengths of the winding portions thereof may be substantially equal to one another. In this case, a plurality of three-dimensional shapes having the same size are formed. Specific circumferential lengths of the outer circumferential surfaces of the respective winding portions 70 to 78 are selectable as appropriate according to the purpose of use of the in vivo indwelling member and the shapes and structures of the middle solid 4A, the large solid 4B, and the anchor portion 40, which are to be formed.

As shown in FIG. 19, in an intermediate shape to be formed by using the mandrel of this example, curved parts 50, 52o to 52s, and 51n to 51s in the primary coil 11, which are curved and extend continuously on substantially the same plane, are formed to have a three-dimensional shape. In this example, two three-dimensional portions, i.e., the three-dimensional portion (large solid 4B) formed by continuously providing at least four curved parts 52o to 52s over four planes; and the three-dimensional portion (middle solid 4A) formed by continuously providing at least four curved parts 51n to 51s over four planes, are formed by the aggregates 7B and 7A of the mandrel 6, respectively.

Then, the primary coil 11 is pushed out into an aneurysm with a relatively small size while placing, on the tip end side, the front end side thereof where the relatively large three-dimensional portion (large solid 4B) is formed, and placing, on the base end side, the rear end side thereof where the relatively small three-dimensional portion (middle solid 4A) is formed. Then, a strong frame is formed by the large three-dimensional portion (large solid 4B) that entered previously. In addition, the smaller three-dimensional portion (middle solid 4A) pushed out later serves as a filling (filler). This reduces a number of steps of a method using the coil, and can reduce burdens on a patient and a doctor.

The length of the primary coil that constitutes the three-dimensional portion excluding the smallest three-dimensional portion, i.e., the large solid 4B in this example, is preferably set to a length of 25% or more and 70% or less of the overall length of the primary coil. In this way, a sufficient amount of the frame is formed by the three-dimensional portion (large solid 4B) pushed out previously, and in addition, the smallest three-dimensional portion (middle solid 4A) pushed out last also serves as the filling sufficiently as described above.

Moreover, with regard to an area ratio between the quadrangle seen from the common axis of the above-mentioned virtual cylindrical body of the middle solid 4A and the quadrangle of the large solid 4B, which is seen in the same way, preferably, the area ratio concerned is set so that the area of the large solid 4B is 1.1 times or more and 2.3 times or less the area of the middle solid 4A. In this way, the middle solid 4A can be loaded in the inside of the frame previously formed by the large solid 4B, and can be caused to sufficiently function as the filling.

The procedure of winding the primary coil around the mandrel is the same as in the example of the above-mentioned representative embodiment, and accordingly, a description thereof will be omitted. Since the winding procedure is the same, also with regard to the intermediate shape to be formed, the large solid 4B including the curved parts 52o to 52s is similar to the middle solid 4A including the curved parts 51a to 51e in the example of the above-mentioned representative embodiment, and the middle solid 4A including the curved parts 51n to 51s is similar to the large solid 4B including the curved parts 52a to 52f of the example of the above-mentioned representative embodiment.

Similar to the example of the above-mentioned representative embodiment, with regard to the four planes of each of the three-dimensional portions, all of the normal directions thereof are perpendicular to a predetermined common axis a1/a2 direction. Each of the curved parts (52o to 52s, 51n to 51s) which constitute the respective three-dimensional portions (large solid 4B, middle solid 4A) is formed in any of the respective planes of the quadrangular virtual cylindrical bodies as seen from the common axes surrounded by the four planes. The intermediate-shape coil of this example is processed into such a secondary shape in which the middle solid 4A is disposed inside the large solid 4B, and the large solid 4B and the middle solid 4A are sequentially developed inside the aneurysm or the like.

Figure 20A:
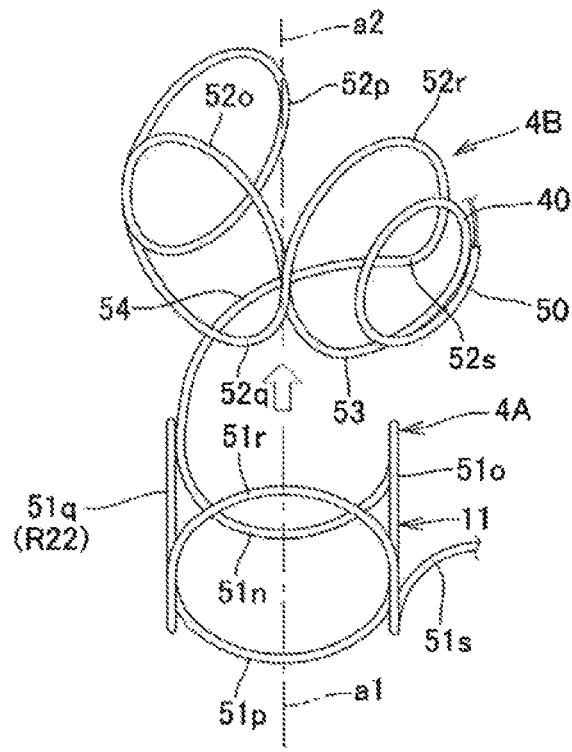
FIG. 20(a) is an explanatory diagram showing a state in which a middle solid and anchor portion of the intermediate-shape coil made by the mandrel according to the modified example are disposed inside a large solid.
Figure 20B:
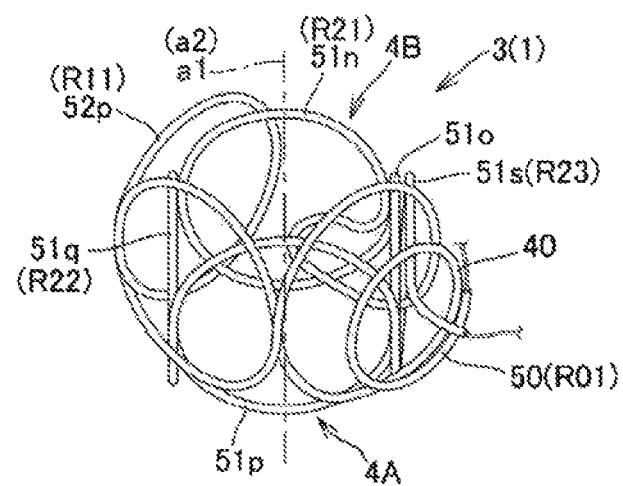
FIG. 20(b) is a perspective view showing a shape of a secondary coil (in vivo indwelling member) having the above disposition.

The intermediate shape is heated in a state of being wound around the mandrel 6, then as shown in FIG. 19, the intermediate-shape coil 2 including the anchor portion 40, the large solid 4B, and the middle solid 4A is obtained, and thereafter, as shown in FIGS. 20(a) and 20(b), the middle solid 4A is disposed inside the large solid 4B. With regard to the disposition, the middle solid 4A and the large solid 4B are disposed and heated so that the axis of the middle solid 4A and the axis of the large solid 4B substantially coincide with each other, and that the planes of the virtual cylindrical bodies thereof are rotated by 45 degrees around the axial center so as not to be parallel to each other. In this way, a secondary shape as shown in FIG. 20(b) is obtained, and the core wire 12 is removed to form the secondary coil, that is, the in vivo indwelling member. When the secondary coil thus disposed is pushed out into the relatively small aneurysm or the like, the relatively small three-dimensional portion is loaded inside the frame previously formed by the largest three-dimensional portion, and can be caused to sufficiently function as the filling. Also with regard to this in vivo indwelling member, the in vivo indwelling member placement device is formed in which the in vivo indwelling member placement wire is connected to the base end side via the coupling member is formed.

FIG. 21 shows still another modified example in which the mandrel 6 described with reference to FIG. 18 is used and the procedure described in FIG. 14 is used as the winding procedure of the primary coil. In FIG. 21 as well, the shape of the secondary coil and the intermediate shape, which are not accompanied by the mandrel, are drawings in which the reinforcement core material (core wire) is inserted in the lumen of the primary coil.

As shown in FIG. 21, in the intermediate shape of this example, curved parts 50, 52t to 52w and 51t to 51w in the primary coil 11, which are curved and extend continuously on substantially the same plane, are formed to have a three-dimensional shape. In this example, two three-dimensional portions, i.e., the three-dimensional portion (large solid 4B) formed by continuously providing at least four curved parts 52t to 52w over four planes; and the three-dimensional portion (middle solid 4A) formed by continuously providing at least four curved parts 51t to 51w over four planes, are formed by the aggregates 7B and 7A of the mandrel 6, respectively.

Then, similar to the example of FIGS. 18 to 20, the primary coil 11 is pushed out into an aneurysm with a relatively small size while placing, on the tip end side, the front end side thereof where the relatively large three-dimensional portion (large solid 4B) is formed, and placing, on the base end side, the rear end side thereof where the relatively small three-dimensional portion (middle solid 4A) is formed. Then, a strong frame is formed by the large three-dimensional portion (large solid 4B) that entered previously. In addition, the smaller three-dimensional portion (middle solid 4A) pushed out later serves as a filling (filler). This reduces a number of steps of a method using the coil, and can reduce burdens on a patient and a doctor.

The length of the primary coil that constitutes the three-dimensional portion excluding the smallest three-dimensional portion, i.e., the large solid 4B in this example, is preferably set to a length of 25% or more and 70% or less of the overall length of the primary coil. In this way, a sufficient amount of the frame is formed by the three-dimensional portion (large solid 4B) pushed out previously, and in addition, the smallest three-dimensional portion (middle solid 4A) pushed out last also serves as the filling sufficiently as described above.

Moreover, with regard to an area ratio between the quadrangle seen from the common axis of the above-mentioned virtual cylindrical body of the middle solid 4A and the quadrangle of the large solid 4B, which is seen in the same way, preferably, the area ratio concerned is set so that the area of the large solid 4B is 1.1 times or more and 2.3 times or less the area of the middle solid 4A. In this way, the middle solid 4A can be loaded in the inside of the frame previously formed by the large solid 4B, and can be caused to sufficiently function as the filling.

The procedure of winding the primary coil around the mandrel is the same as in the example of FIG. 14, and accordingly, a description thereof will be omitted. Since the winding procedure is the same, also with regard to the intermediate shape, the large solid 4B including the curved parts 52t to 52w is similar to the middle solid 4A including the curved parts 51j to 51m of the example of FIG. 15, and the middle solid 4A including the curved parts 51t to 51w is similar to the large solid 4B including the curved parts 52k to 52n of the example of FIG. 15.

Similar to the example of FIGS. 18 to 20, with regard to the four planes of each of the three-dimensional portions, all of the normal directions thereof are perpendicular to a predetermined common axis a1/a2 direction. Each of the curved parts (52t to 52w, 51t to 51w) which constitute the respective three-dimensional portions (large solid 4B, middle solid 4A) is formed in any of the respective planes of the quadrangular virtual cylindrical bodies as seen from the common axes surrounded by the four planes. In addition, the intermediate-shape coil of this example is processed into such a secondary shape in which the middle solid 4A is disposed inside the large solid 4B, and the middle solid 4A and the large solid 4B are sequentially developed inside the aneurysm or the like.

Figure 21A:
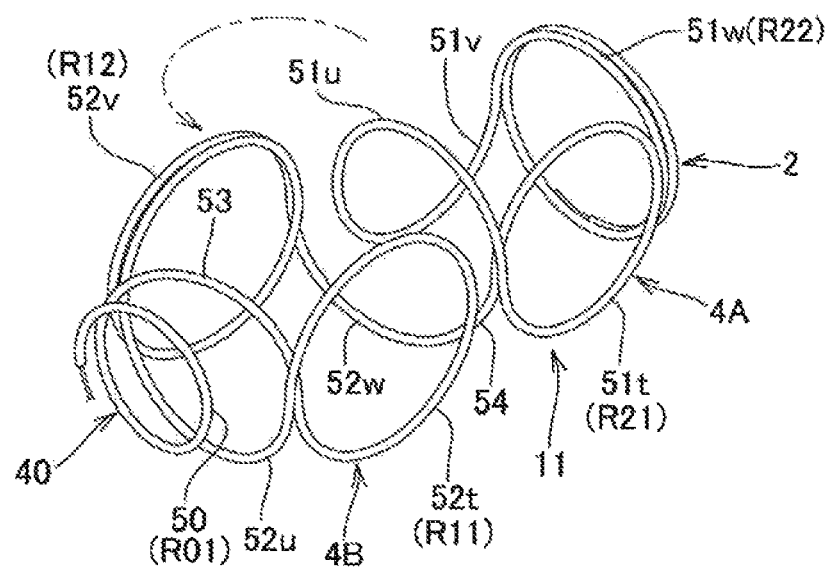
FIG. 21(a) is a perspective view showing a shape of an intermediate-shape coil made by the mandrel of FIG. 18.
Figure 21B:
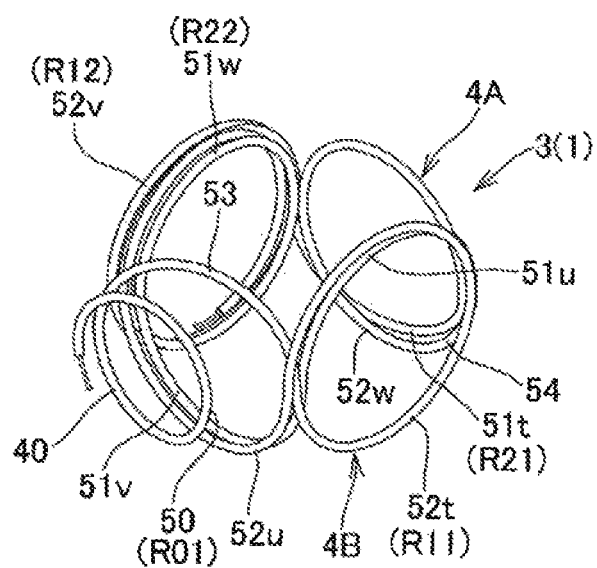
FIG. 21(b) is a perspective view showing a shape of a secondary coil (in vivo indwelling member) in which a middle solid of the intermediate-shape coil is disposed inside a large solid.
Figure 22:
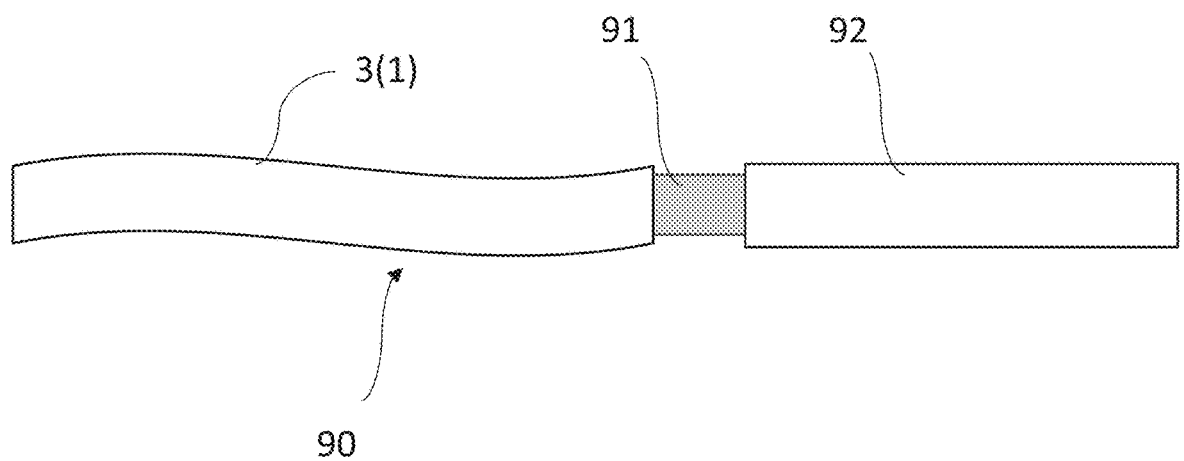
FIG. 22 schematically illustrates an in vivo indwelling member placement device formed of an in vivo indwelling member placement wire and a coupling member.

The intermediate shape is heated in a state of being wound around the mandrel 6, then as shown in FIG. 21(a), the intermediate-shape coil 2 including the anchor portion 40, the large solid 4B, and the middle solid 4A is obtained, and thereafter, similar to the above-mentioned example in FIGS. 18 to 20, as shown in FIG. 21(b), the middle solid 4A is disposed inside the large solid 4B. With regard to the disposition, the middle solid 4A and the large solid 4B are disposed so that the axis of the middle solid 4A and the axis of the large solid 4B substantially coincide with each other, and that the planes of the virtual cylindrical bodies thereof are rotated by 90 degrees around the axial center so as to be parallel to each other. Then, the secondary shape is obtained by heating the intermediate shape, and the core wire is removed therefrom, whereby a secondary coil, that is, an in vivo indwelling member is formed. One of two or more three-dimensional portions may be first placed in the mold, and then another one of the three-dimensional portions may be placed in the one that has been already placed in the mold. Although the rotation angle is set to 90 degrees in this example, the rotation angle is not limited to this. The rotation angle may be other degrees, and the virtual cylindrical bodies may be not rotated (e.g., the rotation angle is substantially zero (0) degree). When the secondary coil thus disposed is pushed out into the relatively small aneurysm or the like, the frame is previously formed by the largest three-dimensional portion, and the relatively small three-dimensional portion is loaded into the inside of the frame to function as the filling. Also with regard to this in vivo indwelling member, the in vivo indwelling member placement device is formed in which the in vivo indwelling member placement wire is connected to the base end side via the coupling member is formed.

While the embodiments of the present invention have been described above, the present invention is not at all limited to these embodiments, and it is a matter of course that the present invention can be implemented in various forms without departing from the spirit of the present invention.

REFERENCE SIGNS LIST

1 In vivo indwelling member
2 Intermediate-shape coil
3 Secondary coil
4A Middle solid
4B Large solid
6 Mandrel
7A, 7B Aggregate
9 Mandrel
10 Wire
11 Primary coil
12 Core wire
40 Anchor portion
50 Curved part
51a to 51w Curved part
52a to 52w Curved part
53 Spiral part
54 Connecting part
60a, 60b Stepped portion
61a, 61b Notch groove
70-78 Winding portion
79, 80 Attachment screw
90 In vivo indwelling member placement device
91 Cuttable coupling member
92 In vivo indwelling member placement wire
a1, a2 Common axis
C1, C2 Virtual cylindrical body
F1 to F4 Plane
F5 to F8 Plane
R01 Loop-shaped part
R11 Loop-shaped part
R21, R22, R23 Loop-shaped part
s1, s2 Quadrangle

The invention claimed is:

1. An in vivo indwelling member having a three-dimensional secondary shape with shape parts of a primary coil, the in vivo indwelling member comprising two or more three-dimensional portions, each three-dimensional portion of the two or more three-dimensional portions being formed by continuously providing at least four of the shape parts over four planes, all of the four planes having normal directions perpendicular to a predetermined common axis direction, each of the at least four shape parts being formed in any of respective planes of a virtual cylindrical body having a shape of a quadrangle as seen from the common axis surrounded by the four planes, and the virtual cylindrical body having openings at a distal end and a proximal end in the common axis, each three-dimensional portion of the two or more three-dimensional portions being set so that areas of the quadrangles as seen from the common of the two or more three-dimensional portions are sequentially changed from a tip end side of the primary coil to a base end side of the primary coil, and a length of the primary coil that constitutes remaining three-dimensional portions excluding one portion of the two or more three-dimensional portions disposed closest to the base end side being set to a length of 25% or more and 70% or less of an overall length of the primary coil, wherein one portion of the two or more three-dimensional portions is disposed inside another portion of the two or more three-dimensional portions, and the common axes are parallel to each other.

2. The in vivo indwelling member according to claim 1, wherein the two or more three-dimensional portions comprise a smaller three-dimensional portion having a smaller area of the quadrangle as seen from the common axis and a larger three-dimensional portion having a larger area of the quadrangle as seen from the common axis, and a ratio of the larger area of the larger three-dimensional portion to the smaller area of the smaller three-dimensional portion is 1.1 to 2.3.

3. The in vivo indwelling member according to claim 1, wherein the two or more three-dimensional portions comprise a smaller three-dimensional portion having a smaller area of the quadrangle as seen from the common axis and a larger three-dimensional portion having a larger area of the quadrangle as seen from the common axis, and a ratio of a length of a shortest side of the quadrangle of the larger three-dimensional portion to a length of a shortest side of the quadrangle of the smaller three-dimensional portion is 1.05 to 1.5.

4. The in vivo indwelling member according to claim 1, wherein one of the two or more three-dimensional portions is smaller than another of the two or more three-dimensional portions, and the common axes of each of the two or more three-dimensional portions are parallel to each other.

5. An in vivo indwelling member having a three-dimensional secondary shape with shape parts of a primary coil, the in vivo indwelling member comprising two or more three-dimensional portions, each three-dimensional portion of the two or more three-dimensional portions being formed by continuously providing at least four of the shape parts over four planes, all of the four planes having normal directions perpendicular to a predetermined common axis direction, each of the at least four shape parts being formed in any of respective planes of a virtual cylindrical body having a shape of a quadrangle as seen from the common axis surrounded by the four planes, and the virtual cylindrical body having openings at a distal end and a proximal end in the common axis, each three-dimensional portion of the two or more three-dimensional portions being set, in order from a tip end side toward a base end side of the primary coil, wherein the two or more three-dimensional portions comprise a smaller three-dimensional portion having a smaller area of the quadrangle as seen from the common axis and a larger three-dimensional portion having a larger area of the quadrangle as seen from the common axis, and a length of the primary coil that constitutes remaining three-dimensional portions excluding the largest three-dimensional portion of the two or more three-dimensional portions being set to a length of 25% or more and 50% or less of an overall length of the primary coil, wherein one portion of the two or more three-dimensional portions is disposed inside another portion of the two or more three-dimensional portions, and the common axes are parallel to each other.

6. The in vivo indwelling member according to claim 5, wherein an anchor portion formed of at least one of the shape parts is provided in a region of the primary coil, the region leading to a tip of the primary coil more on the tip end side than the smallest three-dimensional portion, and a length of the primary coil that constitutes the anchor portion is set to a length of less than 15% of the overall length of the primary coil.

7. An in vivo indwelling member having a three-dimensional secondary shape with shape parts of a primary coil, the in vivo indwelling member comprising two or more three-dimensional portions, each three-dimensional portion of the two or more three-dimensional portions being formed by continuously providing at least four of the shape parts over four planes, all of the four planes having normal directions perpendicular to a predetermined common axis direction, each of the at least four shape parts being formed in any of respective planes of a virtual cylindrical body having a shape of a quadrangle as seen from the common axis surrounded by the four planes, and the virtual cylindrical body having openings at a distal end and a proximal end in the common axis, each three-dimensional portion of the two or more three-dimensional portions being set, in order from a tip end side toward a base end side of the primary coil, wherein the two or more three-dimensional portions comprise a smaller three-dimensional portion having a smaller area of the quadrangle as seen from the common axis and a larger three-dimensional portion having a larger area of the quadrangle as seen from the common axis, and a length of the primary coil that constitutes remaining three-dimensional portions excluding the smallest three-dimensional portion of the two or more three-dimensional portions being set to a length of 25% or more and 70% or less of an overall length of the primary coil, wherein one portion of the two or more three-dimensional portions is disposed inside another portion of the two or more three-dimensional portions, and the common axes are parallel to each other.

8. The in vivo indwelling member according to claim 7, wherein an anchor portion formed of at least one of the shape parts is provided in a region of the primary coil, the region leading to a tip of the primary coil more on the tip end side than the largest three-dimensional portion, and a length of the primary coil that constitutes the anchor portion is set to a length of less than 15% of the overall length of the primary coil.

9. The in vivo indwelling member according to any one of claims 1, 5, and 7, wherein the quadrangles as seen from the common axes of the virtual cylindrical bodies are squares.

10. The in vivo indwelling member according to claim 9, wherein the at least four shape parts are formed in any of the planes which are the squares of each of the virtual cylindrical bodies.

11. An in vivo indwelling member placement device comprising:

an in vivo indwelling member placement wire;

the in vivo indwelling member according to any one of claims 1, 5, and 7; and a cuttable coupling member that couples the wire and the in vivo indwelling member to each other.

12. The in vivo indwelling member placement device according to claim 11, wherein the coupling member is formed of a thermally soluble material.

\* \* \* \* \*